(12) United States Patent
Belgrader et al.

(10) Patent No.: US 8,623,789 B2
(45) Date of Patent: Jan. 7, 2014

(54) INTEGRATED CARTRIDGE

(75) Inventors: Phillip Belgrader, Severna Park, MD (US); Christopher G. Cooney, Severn, MD (US); Aleksandr N. Perov, Germantown, MD (US)

(73) Assignee: Akonni Biosystems, Inc., Frederick, MD (US)

( * ) Notice: Subject to any disclaimer, the term of this patent is extended or adjusted under 35 U.S.C. 154(b) by 271 days.

(21) Appl. No.: 12/886,201

(22) Filed: Sep. 20, 2010

(65) Prior Publication Data
US 2011/0071055 A1 Mar. 24, 2011
US 2012/0004143 A2 Jan. 5, 2012

Related U.S. Application Data

(60) Provisional application No. 61/272,397, filed on Sep. 21, 2009.

(51) Int. Cl.
*G01N 33/00* (2006.01)
(52) U.S. Cl.
USPC ............ 506/39; 422/400; 422/401; 422/68.1
(58) Field of Classification Search
USPC ........................... 506/39; 422/400, 401, 68.1
See application file for complete search history.

(56) References Cited

U.S. PATENT DOCUMENTS

| 2004/0033590 A1 | 2/2004 | Su et al. |
| 2005/0042146 A1 | 2/2005 | Seto |
| 2009/0111193 A1 | 4/2009 | Cooney et al. |

FOREIGN PATENT DOCUMENTS

WO 2007136715 A2 11/2007

OTHER PUBLICATIONS

International Search Report issued in PCT/US2010/002568 dated Apr. 15, 2011.
Written Opinion issued in PCT/US2010/002568 dated Apr. 15, 2011.

*Primary Examiner* — Sam P Siefke
(74) *Attorney, Agent, or Firm* — Andrews Kurth LLP; Michael Ye

(57) ABSTRACT

An integrated cartridge for sample processing and analysis is disclosed. The integrated cartridge contains a sample preparation chamber having a sample inlet and a sample outlet, and a sample purification chamber adapted to receive a replaceable sample purification unit containing a housing and an extraction filter inside the housing. The extraction filter specifically binds to a molecule of interest. The sample purification chamber has a sample inlet that is in fluid communication with the sample outlet of the sample preparation chamber. Also disclosed is a microarray-based sample analysis (MBSA) system.

12 Claims, 29 Drawing Sheets

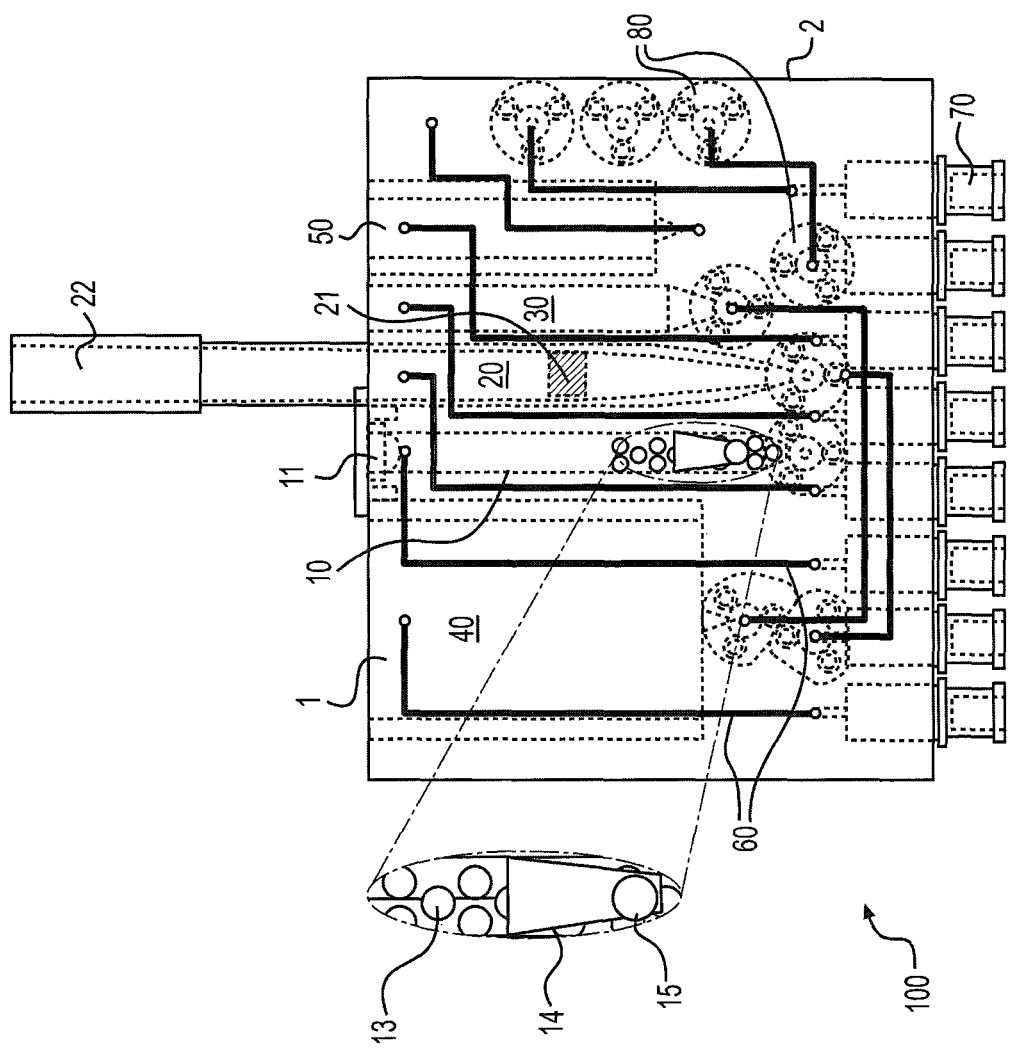

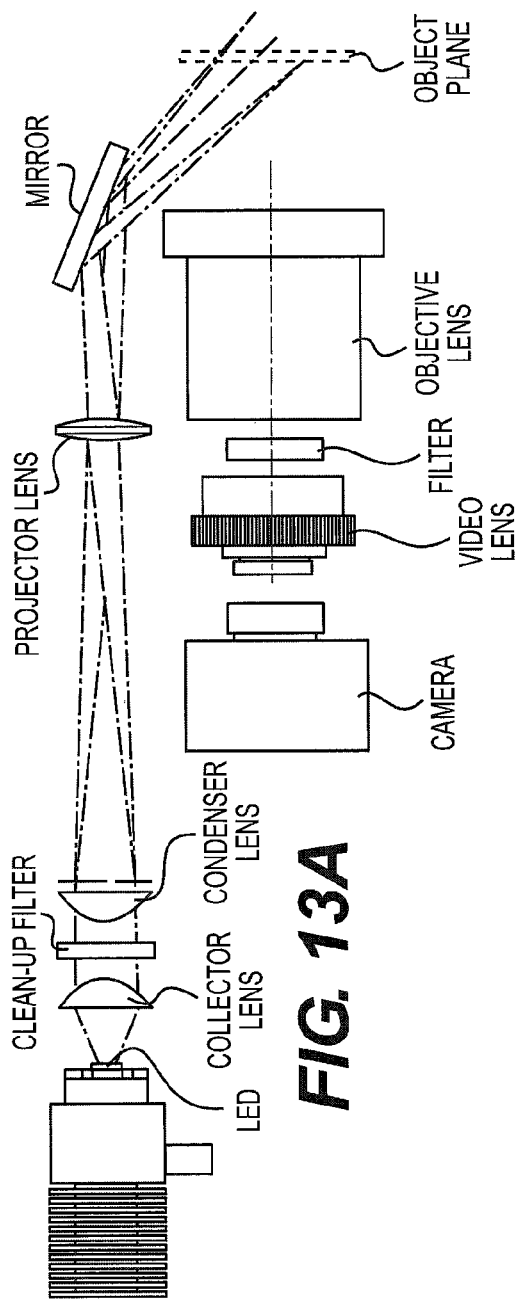
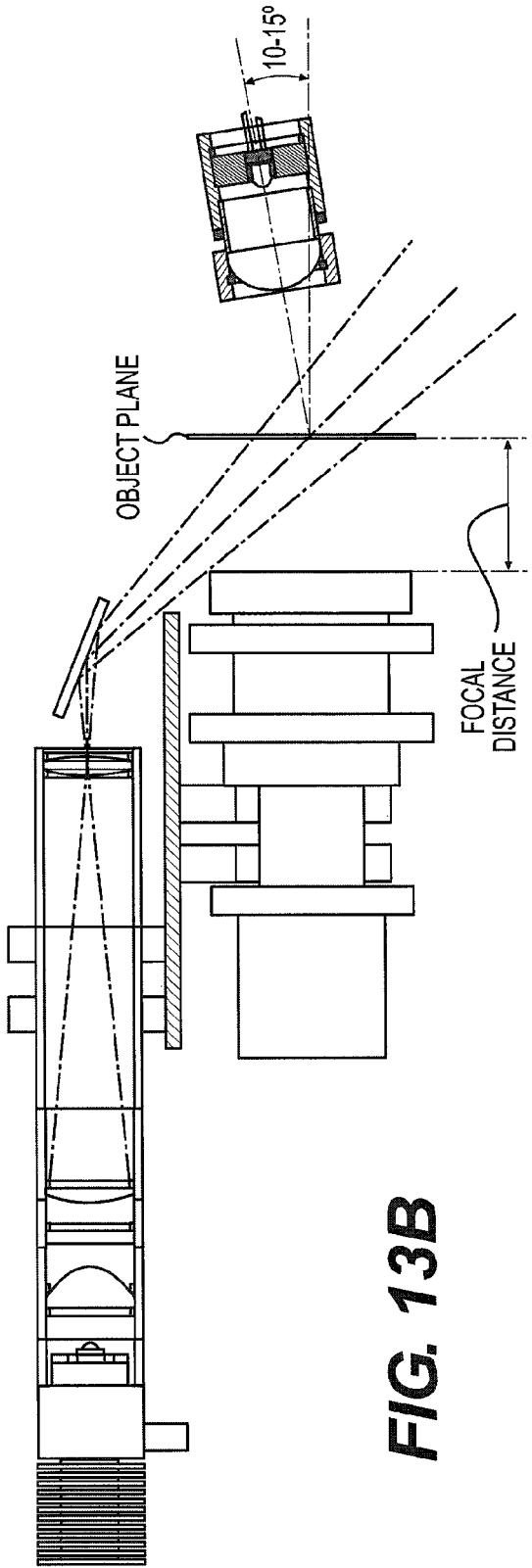
FIG. 13A
FIG. 13B

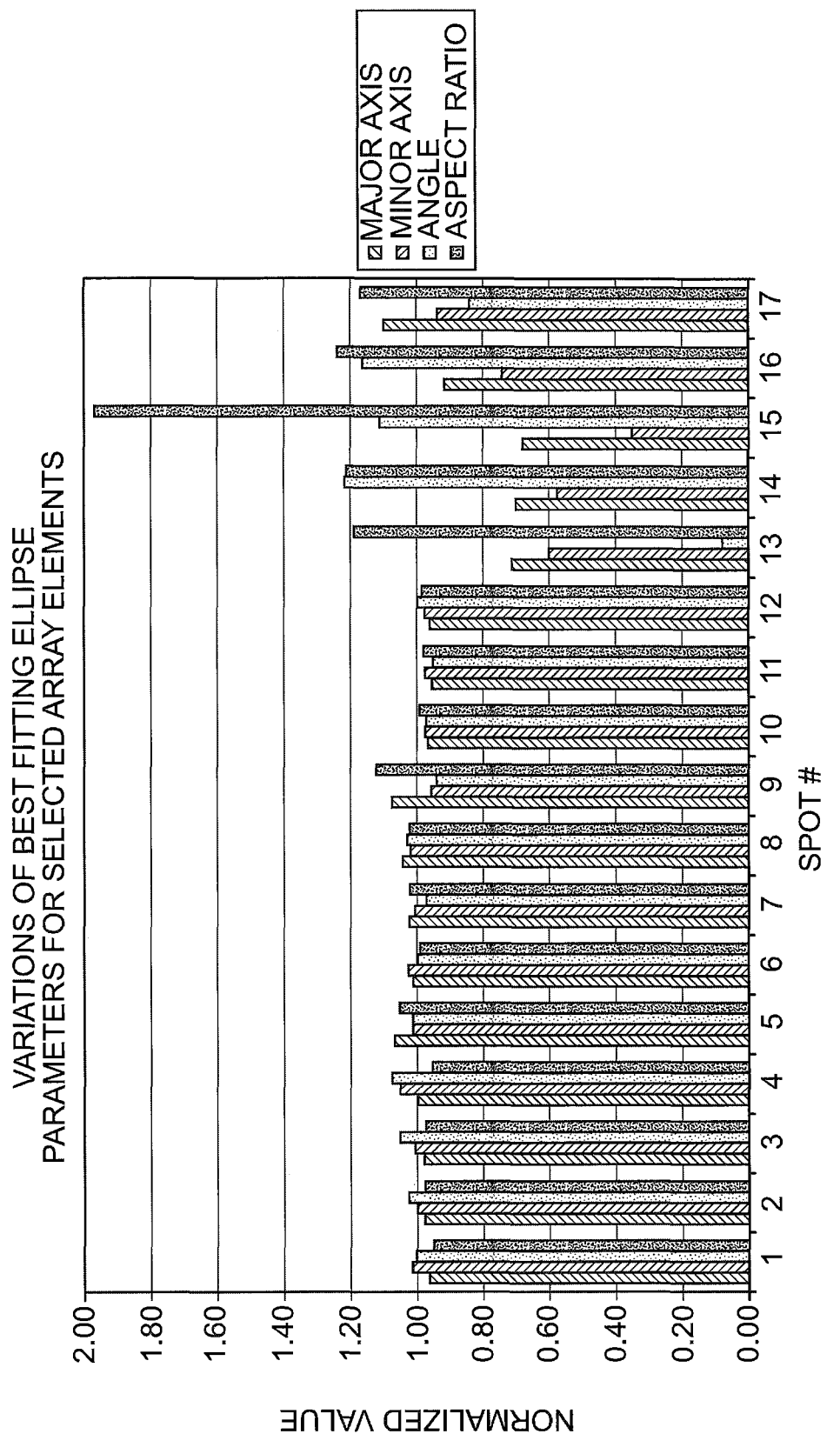

INTEGRATED CARTRIDGE

RELEVANT APPLICATIONS

This application claims the priority of U.S. Provisional Application No. 61/272,397, filed on Sep. 21, 2009, which is incorporated herein by reference in its entirety.

TECHNICAL FIELD

The technical field is biotechnology and, more specifically, methods and apparatus for analysis of biomolecules.

BACKGROUND

It is desirable to have an analytical instrument that possesses both sample preparation and sample analysis functions. It is also desirable to have an analytical instrument that is light and small and can be produced at a low cost. However, microfluidic challenges have impeded the development of such analytical devices. These challenges are due, in part, to the fluid dynamics at small scales. For example, as the diameter of a microfluidic channel decreases, the pressure drop across the channel increases by the $4^{th}$ power, according to the Hagen-Poiseuille equation. When employing complex microfluidic geometries, these large pressure drops can result in flow patterns that are very difficult to predict, particularly with air bubbles in the system. The thermal expansion of air is more than five times greater than liquid, causing additional challenges.

SUMMARY

An integrated cartridge for sample processing and analysis is disclosed. The integrated cartridge contains a sample preparation chamber having a sample inlet and a sample outlet, and a sample purification chamber adapted to receive a replaceable sample purification unit containing a housing and an extraction filter inside the housing. The extraction filter specifically binds to a molecule of interest. The sample purification chamber has a sample inlet that is in fluid communication with the sample outlet of the sample preparation chamber.

Also disclosed is a microarray-based sample analysis (MBSA) system. The MBSA system includes a cartridge holder adapted to receive a detachable cartridge that is configured to receive a detachable, replaceable sample analysis unit having a reaction chamber and a microarray, a fluid control subsystem that controls fluid flow, and an optical subsystem configured to capture an image of the microarray.

BRIEF DESCRIPTION OF DRAWINGS

The detailed description will refer to the following drawings in which:

FIG. 2 is a schematic drawing showing an integrated cartridge with cell lysis means.

FIG. 13A is a schematic showing an embodiment of the optical subsystem with a high-brightness LED.

FIG. 13B is a schematic showing an optical train for fluorescence and FII imaging.

FIGS. 17A and 17B are graphs showing evaluation of morphology for the gel spots in panel A of FIG. 15

DETAILED DESCRIPTION

Figure 1A:
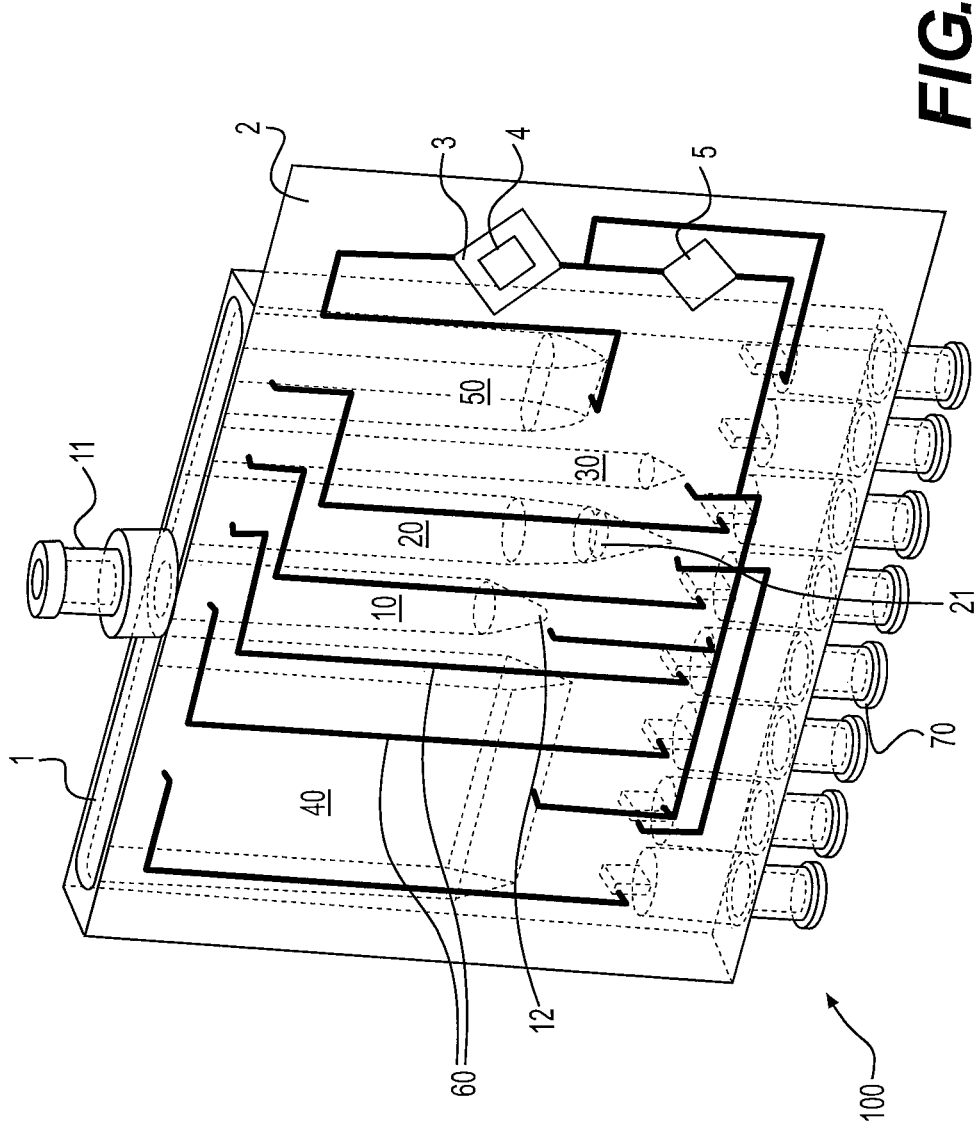
FIGS. 1A and 1B are schematic drawings showing embodiments of the integrated cartridge.

This description is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In the description, relative terms such as "front," "back," "up," "down," "top" and "bottom," as well as derivatives thereof, should be construed to refer to the orientation as then described or as shown in the drawing figure under discussion. These relative terms are for convenience of description and normally are not intended to require a particular orientation. Terms concerning attachments, coupling and the like, such as "connected" and "attached," refer to a relationship wherein structures are secured or attached to one another either directly or indirectly through intervening structures, as well as both movable or rigid attachments or relationships, unless expressly described otherwise.

In describing preferred embodiments of the present invention, specific terminology is employed for the sake of clarity. However, the invention is not intended to be limited to the specific terminology so selected. It is to be understood that each specific element includes all technical equivalents which operate in a similar manner to accomplish a similar purpose.

An integrated cartridge for sample processing and analysis is disclosed. The integrated cartridge includes a sample preparation chamber, a sample purification chamber and a detachable sample analysis unit. The sample preparation chamber has a sample inlet and sample outlet and is in fluid communication with the sample purification chamber. The sample purification chamber contains an extraction filter that specifically binds to a molecule of interest. The detachable sample analysis unit includes at least one sample analysis chamber that contains a microarray.

Figure 1B:
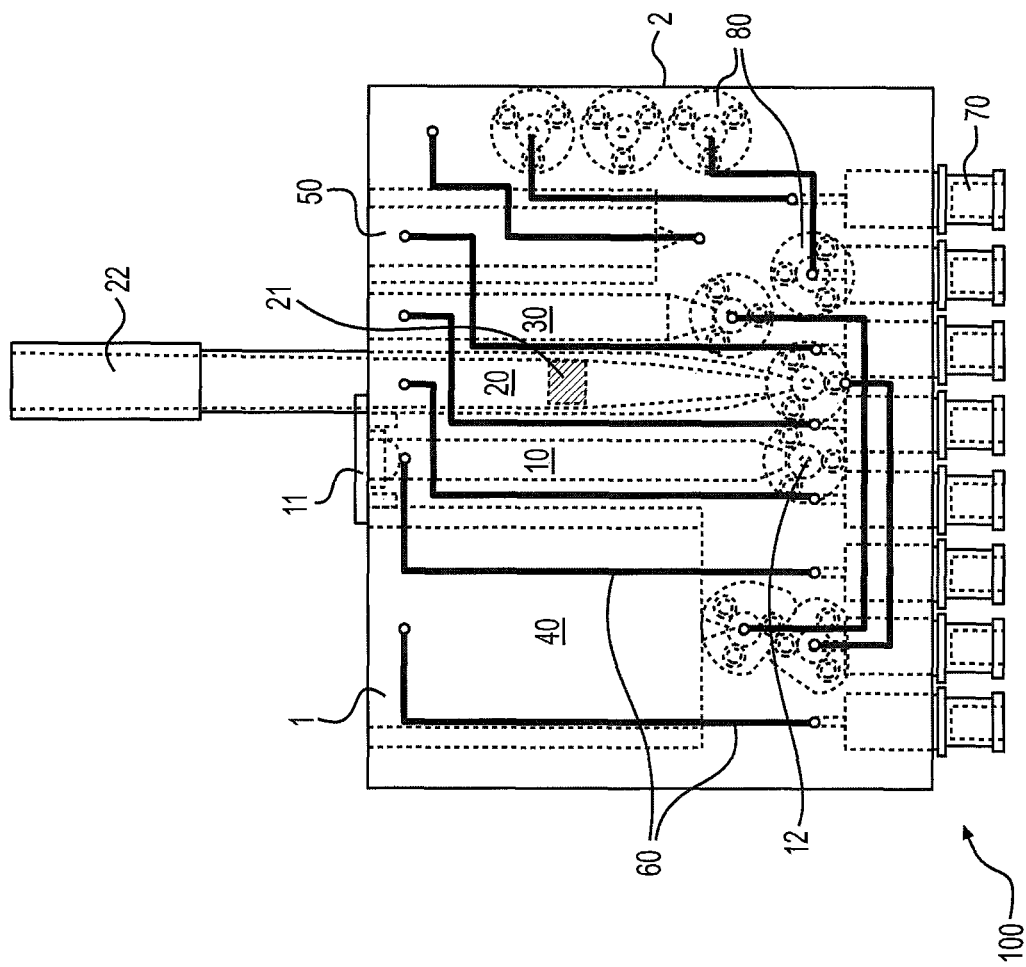

FIG. 1A shows an embodiment of an integrated cartridge. The integrated cartridge allows for the extraction of biomolecules, such as polypeptides and polynucleotides, and subsequent analysis of the biomolecules within the same cartridge. In this embodiment, the integrated cartridge 100 contains a cartridge body 1 and a sample analysis unit 2. The cartridge body 1 contains a sample preparation chamber 10, a sample purification chamber 20 in fluid communication with the sample preparation chamber 10, an sample elution chamber 30 in fluid communication with the sample purification chamber 20, a waste chamber 40 in fluid communication with the sample purification chamber 20, a product waste chamber 50 in fluid communication with the sample analysis unit 2 when it is attached to the cartridge body 1, fluidic channels 60 that connect the chambers to each other, and a fluidic interface 70 that allows the integrated cartridge 100 to be connected to a cartridge base (not shown). In one embodiment, the sample analysis unit 2 is an integrated part of the cartridge body 1. In another embodiment, the sample analysis unit 2 is detachable from the cartridge body 1. FIG. 1B is a schematic drawing showing the same cartridge 100 with on-board valves 80 that control fluid flow in each chamber.

The sample preparation chamber 10 has a sample inlet 11 at an upper portion of the chamber and a sample outlet 12 at a lower portion of the chamber. In the embodiments shown in FIGS. 1A and 1B, the sample inlet 11 is located at the top of the sample preparation chamber 10 and the sample outlet 12 is located at the bottom of the sample preparation chamber 10. In one embodiment, the sample inlet 11 is a dome valve. When connected to a pump, the sample outlet 12 may also serve as an air inlet. Sample mixing inside the sample preparation chamber may be achieved by pumping a gas, such as air or an inert gas (e.g., nitrogen), into the sample preparation chamber 10 from the sample outlet 12. The gas forms bubbles that migrate from the bottom to the top of the chamber 10 and mix the sample during the process.

In another embodiment, the gas is heated to provide a means of uniformly heating the sample/reagent mixture in the sample preparation chamber 10.

The sample purification chamber 20 contains an extraction filter 21 that binds specifically to an analyte. Examples of analytes include, but are not limited to, polynucleotides, polypeptides, lipids, and polysaccharides. In one embodiment, the extraction filter is a silica extraction filter that specifically binds to DNA. In another embodiment the extraction filter is a porous material that specifically binds to a protein. In one embodiment, the extraction filter 21 is located in a removable sample purification unit 22 that can be easily detached from the cartridge body 1 and replaced with a new sample purification unit 22. The sample purification unit 22 comprises a housing with an inlet and an outlet, and an extraction filter 21 that specifically binds to an analyte. In one embodiment, the sample purification unit 22 is in the form of a pipet tip. In a preferred embodiment, the pipet tip is sized to fit within the confines of the sample purification chamber 20. In another preferred embodiment, the extraction filter 21 is the glass frit described in U.S. patent application Ser. Nos. 11/933,113 and 12/213,942, both of which are herein incorporated by reference in their entirety.

The elution chamber 30 is connected to both the sample purification chamber 20 and sample analysis unit 2 when it is attached to the cartridge body 1. In certain embodiments, the elution chamber 30 is eliminated from the integrated cartridge and the sample purification chamber 20 is connected directly to the sample analysis unit 2.

The integrated cartridge 100 is designed to operate in the upright position as shown in FIGS. 1A and 1B. The sample preparation chamber and sample purification chamber are are designed to have a diameter that is sufficient to allow bubbles to rise to the top.

The sample analysis unit 2 may contain one or more chambers for sample analysis. In one embodiment, the sample analysis unit 2 contains a microarray chamber 3 that contains a microarray 4 for the analysis of the analyte. The microarray 4 can be a microarray of any type. In one embodiment, the microarray 4 is a DNA array. In another embodiment, the microarray 4 is a protein or peptide array. In another embodiment, the microarray is a gel element array described in e.g., U.S. Pat. Nos. 5,741,700, 5,770,721, 5,981,734, and 6,656, 725, and U.S. patent application Ser. Nos. 10/068,474, 11/425,667 and 60/793,176, which are hereby incorporated by reference in their entirety. In yet another embodiment, the microarray 4 is an antibody array.

In one embodiment, the microarray chamber 3 also serves as a reaction chamber for an amplification reaction, such as polymerase chain reaction (PCR) or arrayed-primer extension (APEX).

In another embodiment, the sample analysis unit 2 further contains an amplification chamber 5. In one embodiment, the amplification chamber 5 is a PCR chamber that can be heated and cooled repetitively to amplify a DNA target inside the amplification chamber 5.

The sample analysis unit 2 and/or the cartridge body 1, are made from materials capable of withstanding thermocycling, and immune to solvents such as ethanol. The cartridge body can be machined or injection molded.

In one embodiment, the microarray chamber 3 and/or the amplification chamber 5 have a hydrophilic interior surface. In a preferred embodiment, the microarray chamber 3 and/or the amplification chamber 5 are hydrophilic flow cells described in U.S. patent application Ser. No. 12/149,865, which is incorporated herein by reference in its entirety.

During operation, the cartridge 100 is inserted into a fluidic docking station. In one embodiment, fluidic docking station engages with the cartridge 100 through luer tapered bosses that activate luer-activated valves on the cartridge. A sample, such as a cell suspension, is loaded into the sample preparation chamber 10 of the integrated cartridge 100 through the sample inlet 11. A cell lysis buffer is added to the sample preparation chamber 10, and mixed with the sample by air bubbles that migrate from the bottom to the top of the sample preparation chamber 10. The air bubbles are controlled by regulated air flow from an air pump. This air may be heated for protocols that require incubation at an elevated temperature. The mixed sample is then introduced into the sample purification chamber 20, which contains the extraction filter 21 that specifically binds to the analyte of interest. The sample passes through the extraction filter 21 to allow the analyte of interest to bind to the extraction filter 21. In certain embodiments, the sample is cycled back and forth across the extraction filter 21 a number of times to improve efficiency of analyte binding. The unbound sample is then directed to the waste chamber 40 through on-board cartridge pin valves 80 and fluidic channels 60. Leaving the waste in the cartridge prevents contamination with subsequent samples.

The extraction filter 21 is washed with a wash buffer one or more times. Used wash buffer is directed to the waste chamber 40 through on-board cartridge valves 80 and fluidic channels 60. In one embodiment, the wash buffer is an ethanol-based wash buffer and is cycled 5 times through the extraction filter 21. An elution buffer is then introduced into the sample purification chamber 20 through the extraction filter 21. The eluted analyte is directed into the elution chamber 30, which removes the bubbles in the eluant. The eluted analyte is then used for the subsequent sample analysis in the sample analysis unit. Aliquots of the eluted analyte may also be removed for other types of analysis. In one embodiment, an eluted DNA sample is directed into the amplification chamber 5 for PCR amplification. Temperature change in the amplification chamber 5 may be achieved by oscillating two temperature fluids through flexible bladders that makes intimate contact with the amplification chamber 5, as described, for example, in described in U.S. patent application Ser. Nos. 11/843,843 and 12/232,669, which are incorporated herein by reference in their entirety. The on-board cartridge valves 80 switch between thermally-controlled reservoirs to provide a rapid change in temperature. The amplification product is directed into the microarray chamber for hybridization to the microarray.

Integrated Cartridge with Cell Lysis Beads

In certain embodiments, the sample preparation chamber 10 further includes sample lysis means for lysing cell samples. In an embodiment shown in FIG. 2, the sample preparation chamber 10 contains a plurality of cell lysis beads 13 and a magnetic stirring element 13 with a magnet 15. A suspension of intact cells is added to the sample preparation chamber 10 and a rotating magnetic field is applied to the sample preparation chamber 10 to rotate the magnetic stirring element 13 at a rotation speed sufficient to lyse the cells.

As used herein, the term "cell" refers to eukaryotic cells, prokaryotic cells, and components or fragments thereof. The term "cell" includes parasites, bacteria, bacteria spores, fungi, virus particles, as well as an aggregation of cells such as multi-cell organisms, tissues and fragments thereof. The term "cell suspension" refers to a mixture of cells and a liquid medium, wherein the cells are suspended in the liquid medium. Preferably, the cells are suspended at a concentration that is not too thick or viscous to interfere with the movement of the magnetic stir element.

In a certain embodiment, eukaryotic or prokaryotic cells are suspended in the concentration range of $1\times10^2$ to $1\times10^5$ cells/ml. In another embodiment, eukaryotic or prokaryotic cells are suspended in the concentration range of $1\times10^3$ to $1\times10^4$ cells/ml. In other embodiment, virus particles are suspended in the concentration range of $1\times10^7$ to $1\times10^{13}$ particles/ml. In yet other embodiment, virus particles are suspended in the concentration range of $1\times10^9$ to $1\times10^{11}$ particles/ml.

The liquid medium can be isotonic, hypotonic, or hypertonic. In some embodiments, the liquid medium is aqueous. In certain embodiments, the liquid medium contains a buffer and/or at least one salt or a combination of salts. In some embodiments, the pH of the liquid medium ranges from about 5 to about 8, from about 6 to 8, or from about 6.5 to about 8.5. A variety of pH buffers may be used to achieve the desired pH. Suitable buffers include, but are not limited to, Tris, MES, Bis-Tris, ADA, ACES, PIPES, MOPSO, Bis-Tris propane, BES, MOPS, TES, HEPES, DIPSO, MOBS, TAPSO, HEPPSO, POPSO, TEA, HEPPS, Tricine, Gly-Gly, Bicine, and a phosphate buffer (e.g., sodium phosphate or sodium-potassium phosphate, among others). The liquid medium may comprise from about 10 mM to about 100 mM buffer, about 25 mM to about 75 mM buffer, or from about 40 mM to about 60 mM buffer, among others. The type and amount of the buffer used in the liquid medium can vary from application to application. In some embodiments, the liquid medium has a pH of about 7.4, which can be achieved using about 50 mM Tris buffer. In some embodiments the liquid medium is water.

The cell lysis beads can be any particle-like or bead-like material that has a hardness greater than the hardness of the cells to be lysed. The cell lysis beads may be made of plastic, glass, ceramics, or any other non-magnetic materials, such as non-magnetic metal beads. In one embodiment, the cell lysis beads are rotationally symmetric to one axis (e.g., spherical, rounded, oval, elliptic, egg-shaped, and droplet-shaped particles). In other embodiments, the cell lysis beads have polyhedron shapes. In other embodiments, the cell lysis beads are irregular shaped particles. In yet other embodiments, the cell lysis beads are particles with protrusions.

In one embodiment, the cell lysis beads have diameters in the range of 10-1,000 μm. In other embodiments, the cell lysis beads have diameters in the range of 20-400 μm. In yet other embodiments, the cell lysis beads have diameters in the range of 50-200 μm.

The magnetic stir element can be of any shape and has dimensions that match the container. In other words, the magnetic stir element should be small enough to be placed into the container and to spin or stir within the container. It is within the knowledge of a person of ordinary skill in the art to choose a magnetic stir element of appropriate sizes for a given container. The magnetic stir element can be a bar-shaped, cylinder-shaped, rod-shaped, cross-shaped, V-shaped, triangular, rectangular or disc-shaped stir element. In one embodiment, the magnetic stirring element has a rectangular shape. In another embodiment, the magnetic stirrer has a two-pronged tuning fork shape. In yet another embodiment, the magnetic stirrer has a V-like shape. In certain embodiments, the magnetic stir element is coated with a chemically inert material, such as plastics, glass or porcelain.

In one embodiment, the cell lysis beads 13 and/or the magnetic stirring element 13 are pre-packed into the sample preparation chamber 10. In another embodiment, the cell lysis beads 13 and/or the magnetic stirring element 13 are pre-packed into a removable sample lysis unit that can be easily placed into the sample preparation chamber 10 and discarded after cell lysis. In yet another embodiment, the cell lysis beads 13 and/or the magnetic stirring element 13 are added to the sample preparation chamber 10 with the cell suspension. The cell lysis beads 13, the magnetic stirring element 13 and the cell suspension may be placed into the sample preparation chamber 10 in any order. In one embodiment, the cell suspension is loaded into the sample preparation chamber 10 first and followed with either the cell lysis beads or the magnetic stirring element. In another embodiment, the hard beads and/or the magnetic stirring element are placed into the sample preparation chamber 10 first, followed with the cell suspension.

The cartridge is then placed in close proximity to a magnetic stirrer. The cell suspension is stirred with the magnetic stirring element at a rotation speed sufficient to lyse the cells inside the container. The optimal stirring speed and duration can be empirically determined based on the cells, viruses or tissues to be lysed. The appropriate rotation speed is application dependent and can be determined by a person of ordinary skill in the art. Generally speaking, the rotational speed sufficient to lyse the cells is determined by factors such as the type of cells, the concentration of cell suspension, the size and shape of the magnetic stirring element, the amount, size, shape and hardness of the hard beads, and the size, shape and interior surface roughness of the container. In certain embodiments, the container in the shape of a test tube or Eppendorf tube is placed in a rack on a standard laboratory magnetic stirrer plate and is stirred at the highest speed setting.

In certain embodiments, lysing of particular cell types can be facilitated by adding additives to the cell suspension prior to the stirring step. Examples of additives include enzymes, detergents, surfactants and other chemicals such as bases and acids. It has been found that alkaline conditions (e.g. 10 mM NaOH) may enhance the lysis efficiency for certain types of cells. It should be noted, however, that the additive should not interfere with the downstream reactions in the sample analysis process. The cell suspension may also be heated during stirring to enhance the lysis efficiency.

Other embodiments of the bead/magnetic stirrer lysis methods and systems are described in U.S. Provisional Application No. 61/272,396, which is incorporated herein by reference in its entirety.

Besides the bead/magnetic stirrer method, cells in the sample preparation chamber 10 may be lysed with other methods such as bead beating, vortexing, sonication and chemical lysis.

To avoid problems commonly associated with microfluidic devices, the integrated cartridge may contain one or more of the following features (1) The microfluidic channels in the integrated cartridge are sufficiently large (0.2-1 mm, preferably 0.5 mm in diameter) to reduce backpressure and enable reproducible injection molded features, which can be highly variable when creating microfluidic geometries below 0.1 mm (2) The interior surface of the microfluidic channels are fully covered, or partially covered or coated with a hydrophilic film to reduce bubble trapping inside the microfluidic channels. (3) The reaction chambers (i.e., the sample preparation chamber, the sample purification chamber and the sample elution chamber) in the integrated cartridge are designed in a vertically-oriented tower shape to ensure that bubbles rise to the top of the chamber due to the density difference of air compared with water. The tower design also allows for sample mixing in the tower by flowing air into the sample from the bottom of the tower. The liquid is vigorously mixed by the air bubbles rising from the bottom to the top. (5) The extraction filter in the integrated cartridge has a large porosity to minimize back pressure. (6) The on-board cartridge valves in the integrated cartridge shut off fluidic pathways and prevent liquids from flowing in unwanted paths. (7) The cartridge is designed so that the liquid is controlled by precision pumps and selection valves off the disposable cartridge. The liquid metering occurs on volumes greater than 10 μL, to prevent small air bubbles from causing large variations in reagent proportions.

Examples of the hydrophilic material that can be used for the hydrophilic cover or coating include, but are not limited to, hydrophilic polymers such as poly(N-vinyl lactams), poly(vinylpyrrolidone), poly(ethylene oxide), poly(propylene oxide), polyacrylamides, cellulosics, methyl cellulose, polyanhydrides, polyacrylic acids, polyvinyl alcohols, polyvinyl ethers, alkylphenol ethoxylates, complex polyol mono-esters, polyoxyethylene esters of oleic acid, polyoxyethylene sorbitan esters of oleic acid, and sorbitan esters of fatty acids; inorganic hydrophilic materials such as inorganic oxide, gold, zeolite, and diamond-like carbon; and surfactants such as Triton X-100, Tween, Sodium dodecyl sulfate (SDS), ammonium lauryl sulfate, alkyl sulfate salts, sodium lauryl ether sulfate (SLES), alkyl benzene sulfonate, soaps, fatty acid salts, cetyl trimethylammonium bromide (CTAB) a.k.a. hexadecyl trimethyl ammonium bromide, alkyltrimethylammonium salts, cetylpyridinium chloride (CPC), polyethoxylated tallow amine (POEA), benzalkonium chloride (BAC), benzethonium chloride (BZT), dodecyl betaine, dodecyl dimethylamine oxide, cocamidopropyl betaine, coco ampho glycinate alkyl poly(ethylene oxide), copolymers of poly(ethylene oxide) and poly(propylene oxide) (commercially called Poloxamers or Poloxamines), alkyl polyglucosides, fatty alcohols, cocamide MEA, cocamide DEA, cocamide TEA. Surfactants can be mixed with reaction polymers such as polyurethanes and epoxies to serve as a hydrophilic coating.

Simplified Integrated Cartridge

Also disclosed is a simplified cartridge for sample processing. The cartridge includes a sample preparation chamber having an inlet and an outlet and a sample purification chamber having an inlet and an outlet. The sample preparation chamber contains a magnetic stir element and a plurality of cell lysis beads disposed therein. The sample purification chamber contains an extraction filter and is in fluidic communication with the sample preparation chamber.

In one embodiment, the magnetic stir element and the plurality of cell lysis beads are pre-packed in a container that can be easily inserted or removed from the sample preparation chamber and the extraction filter is pre-packed in a container that can be easily inserted or removed from the sample purification chamber.

Dual-Function Integrated Cartridge

Also disclosed is a dual-function cartridge that contains both protein and nucleic acid purification capabilities. Briefly, the dual-function cartridge contains a nucleic acid purification module and a protein purification module. Each module contains a sample purification chamber and a sample elution chamber. In one embodiment, the modules share a single sample preparation chamber and/or a single waste chamber. In another embodiment, the modules share a single sample preparation chamber, but each module contains its own waste chamber. In yet another embodiment, each module has its own sample preparation chamber and waste chamber. Appropriate cartridge base setup can be constructed to allow simultaneous purification of nucleic acid and protein or serial purification of nucleic acid and protein.

Figure 3A:
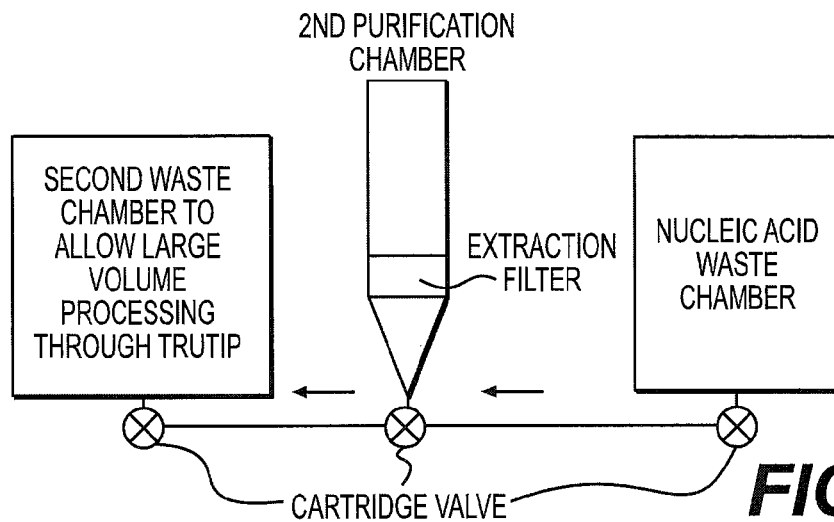
FIG. 3A-3C are schematics showing different embodiments of the protein purification components of a dual-function integrated cartridge.

In one embodiment, a sample is processed in a serial fashion. As shown in FIG. 3A, the sample is processed for nucleic acid purification first. The nucleic acid-deprived sample in the nucleic waste chamber is aspirated into a second purification chamber (e.g., a TruTip) for protein purification and is then dispensed into a second waste chamber. The reagents are driven by a bi-directional pump such as the milliGAT pump. Protein washing buffer may be added directly to the second purification chamber from the buffer reservoir (not shown).

Figure 3B:
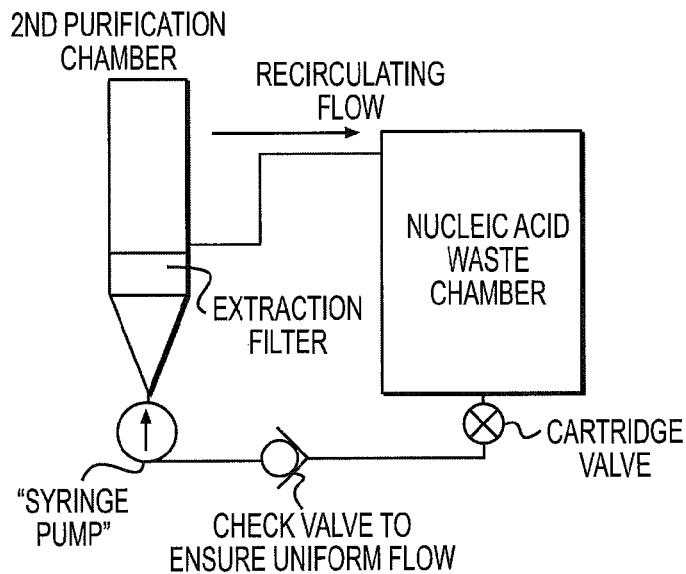

In another embodiment, the integrated cartridge is modified so that the cartridge valve on the second purification chamber may serve as a syringe-type pump. As shown in FIG. 3B, only a single waste chamber is needed. Specifically, the cartridge is modified to have a reservoir pocket connected to the cartridge valve on the second purification chamber (shown as the "syringe pump" in FIG. 3B), so that liquid in the nucleic acid waste chamber may fill the reservoir pocket (similar to filling the barrel of a syringe) during the "withdraw" state of the "syringe pump", and flow into the second purification chamber during the "dispense" state of the "syringe pump." The size of the reservoir pocket may vary depending on the size and function of the integrated cartridge. In certain embodiments, the reservoir has a volume of 0.01-10 ml, 0.2-5 ml, 0.5-3 ml, or 1-5 ml. The shape and exact location of the reservoir may be adjusted based on the overall design of the integrated cartridge. A check valve is installed between the nucleic acid waste chamber and the second purification chamber to ensure unidirectional flow of the liquid. The washing step in the second purification chamber can be accomplished by closing the cartridge valve, open vent (not shown) in the nucleic acid waste chamber and continuously flow the protein washing buffer from the buffer reservoir into the second purification chamber through the "syringe pump."

Figure 3C:
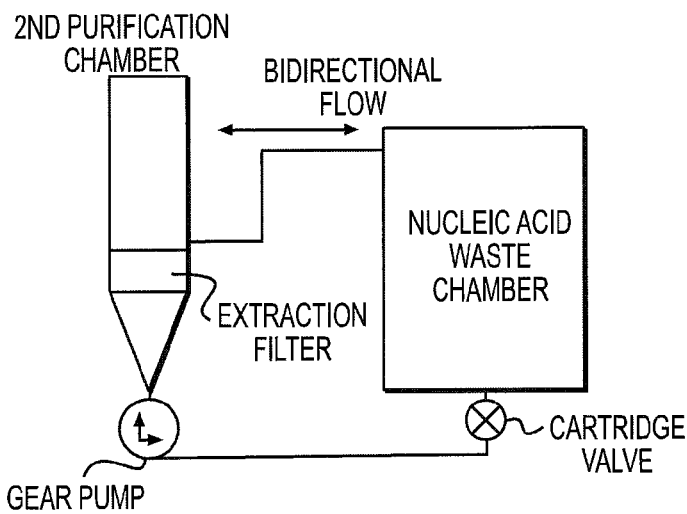

In yet another embodiment, the second purification chamber is attached to a gear pump that continuously recirculates solution through the frit in the second purification chamber (FIG. 3C). The gear pump can operate bi-directionally and no check valve is needed between the nucleic acid waste chamber and the second purification chamber. The protein washing step may be accomplished by closing the cartridge valve, opening the vent in the nucleic acid waste chamber and continuously flowing the protein wash buffer from the buffer reservoir into the second purification chamber through the gear pump.

The Microarray-Based Sample Analysis (MBSA) System

Figure 4:
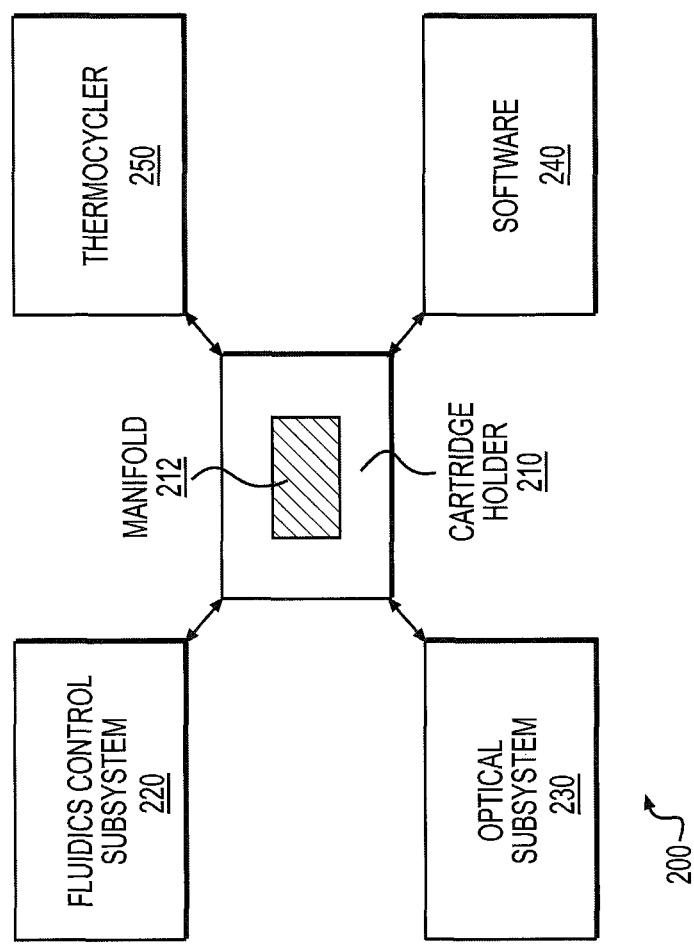
FIG. 4 is a block diagram of a microarray-based sample analysis (MBSA) system.

Also disclosed is a microarray-based sample analysis (MBSA) system. As shown in FIG. 4, an embodiment of the MBSA system 200 includes a cartridge holder 210, a fluid control subsystem 220, an optical subsystem 230, control software 240 and, optionally, a thermocycler 250.

The cartridge holder 210 is configured to be connected to an integrated cartridge 100 through a fluidic manifold 212. The cartridge holder 210 also holds the integrated cartridge 100 in a position to facilitate interaction between various components of the integrated cartridge and the subsystems of the MBSA system. For example, a properly attached cartridge would position the PCR chamber 5 of the cartridge between the heating elements of the thermocycler 250 and allow optical interrogation of the microarray 4 by the optical subsystem.

The fluid control subsystem 220 controls the fluid movement within the MBSA system 200. The subsystem includes multiple fluid containers, pumps, valves and tubings. The fluid control subsystem 220 is directly connected to the integrated cartridge 100 through the fluidic manifold 212

The optical subsystem 230 is designed to capture images of the microarray 4 of the sample analysis unit 2 after hybridization to a sample. In certain embodiments, the optical subsystem is specifically designed for low-level fluorescence detection on microarrays. In one embodiment, the optical subsystem uses confocal or quasi-confocal laser scanners that acquire the microarray image pixel by pixel in the process of interrogating the object plane with a tightly focused laser beam. The laser scanners offer the advantages of spatially uniform sensitivity, wide dynamic range, and efficient rejection of the out-of-focus stray light. The laser scanners, however, are very delicate and expensive devices.

In another embodiment, the optical subsystem uses imaging devices with flood illumination, in which all the microarray elements (features) are illuminated simultaneously, and a multi-element light detector, such as a CCD camera, acquires the image of microarray either all at once or in a sequence of a few partial frames that are subsequently stitched together. Compared to laser scanners, CCD-based imaging devices have simpler designs and lower cost. CCD-based imaging systems are an attractive option for both stand-alone and built-in readers in cost-sensitive applications relying on microarrays of moderate complexity (i.e., having a few hundred or fewer array elements). Commercial instruments typically use cooled CCD cameras and employ expensive custom-designed objective lenses with an enhanced light-collection capability that helps to balance, to some extent, the low efficiency of the excitation scheme.

In another embodiment, the optical subsystem contains an imaging device that uses a non-cooled CCD camera. Although non-cooled cameras typically have a noticeably higher dark current as compared to the cooled models, the optical subsystem could provide the required sensitivity without using exposures in excess of a few seconds by (1) increasing the excitation intensity, or (2) employing an objective lens with high light collection efficiency; or (3) using the above two approaches in combination. The light source can be a conventional light source, such as a metal halide or mercury bulb, a laser-based system, or a high-intensity LED.

In another embodiment, the optical subsystem has a fluorescence-independent imaging (FII) mode as a supplementary imaging mode of microarray reader operation. The FII mode allows imaging the array elements regardless of their fluorescence level.

The practical implementation of FII is technically challenging in both microarray scanners and imagers using flood illumination. The problem is especially difficult when the microarrays to be imaged are the mainstream planar arrays, because the layer of biomolecular probes immobilized on the microarray substrate is too thin to produce a noticeable change in the intensity of light used for probing the slide surface.

In one embodiment, the present invention uses dark field illumination in reflected light for imaging gel arrays printed on opaque (black) plastic substrates. In another embodiment, the present invention uses oblique illumination in transmitted light for imaging gel arrays printed on transparent (glass) slides. In both cases, the light source used for FII could be any light source emitting within the transmission band of the reader's emission filter.

The control software 240 is designed to control all the components of the MBSA system, including the fluid control subsystem 220, the optical subsystem 230, the thermocycler 250 and any additional subsystems. The control software 240 may be installed on any computer that is connected to the MBSA system and provides a user interface for the MBSA system. In one embodiment, the MBSA system includes a controller that contains a processor, memory, and a user interface The thermocycler 250 is configured to provide heating and cooling to the PCR chamber 5 of the integrated cartridge 100. In one embodiment, the thermocycler 250 is a bladder thermocycler described in U.S. patent application Ser. Nos. 11/843,843 and 12/232,669, both of which are herein incorporated by reference in their entirety.

In another embodiment, the MBSA system further includes an isothermal heating system for the microarray chamber 3. In one embodiment, the isothermal heating system contains an air heating unit and a blower that blows heated air through a nozzle to the back side of the microarray chamber. Thermal control is achieved with a thermocouple at the nozzle or near the microarray chamber.

In another embodiment, the microarray chamber is heated by a single sided bladder so that the microarray chamber can be imaged with the optical system from the other side. This embodiment would allow real-time PCR monitoring of the gel-elements in the array as described elsewhere (Khodakov et al., BioTechniques, (2008) 44:241-248).

In another embodiment, the MBSA system further includes a cell lysis subsystem. In one embodiment, the cell lysis subsystem includes a magnetic stirrer that produces a rotating magnetic field. In another embodiment, the cell lysis subsystem produces sonication or vibration to the integrated cartridge to facilitate cell lysis.

EXAMPLES

Example 1

Components of the Microarray Based Sample Analysis (MBSA) System

A. The Fluidic Subsystem

Figure 5:
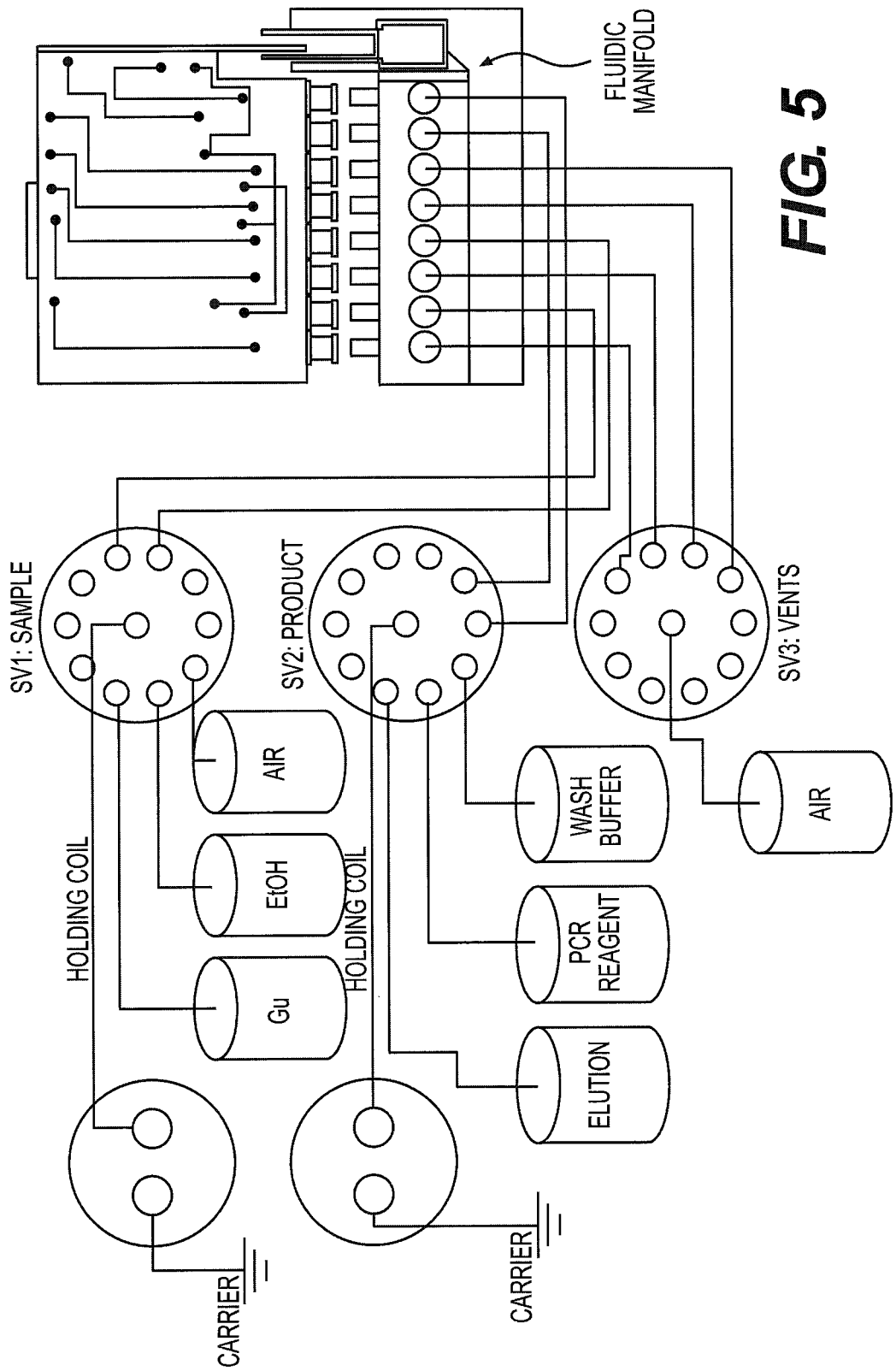
FIG. 5 is a schematic of the fluidic subsystem showing pumps and selection valves (SV) connected to the integrated cartridge.

The fluidic subsystem consists of three types of functional components: bidirectional microfluidic pumps, selection valves, and cartridge "pin" valves. FIG. 5 is a schematic of the fluidic subsystem showing pumps and selection valves connected to the integrated cartridge. The fluidic layout uses a combination of bidirectional pumps and selection valves, available from Global FIA. As shown in FIG. 5, the fluidic subsystem is connected to the integrated cartridge through a fluidic manifold 90 and keeps the various reagents in storage containers outside the integrated cartridge 100.

Figure 6B:
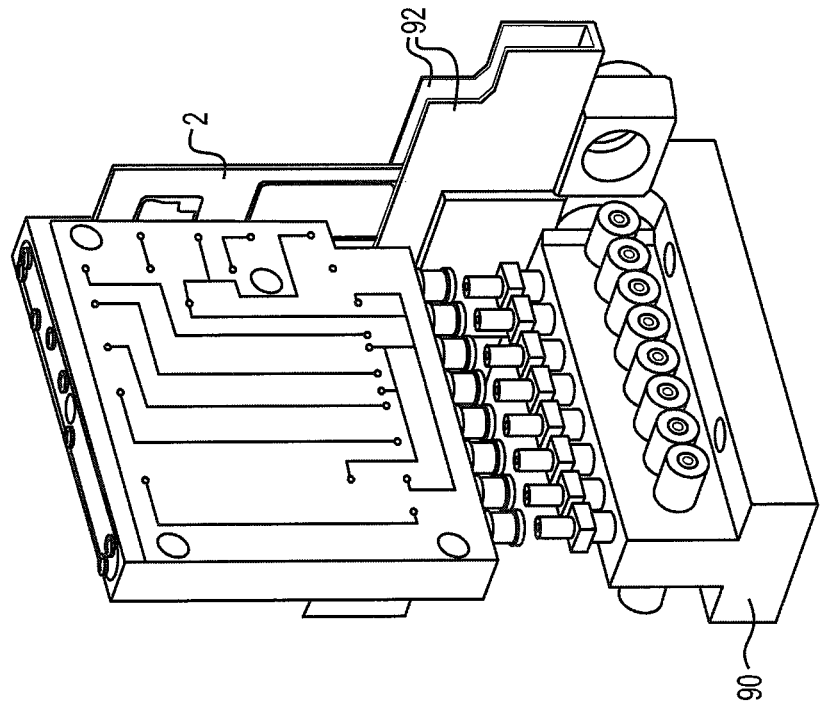
FIG. 6B is a schematic showing an integrated cartridge residing in a fluidic manifold with the thermocycler bladders.
Figure 6A:
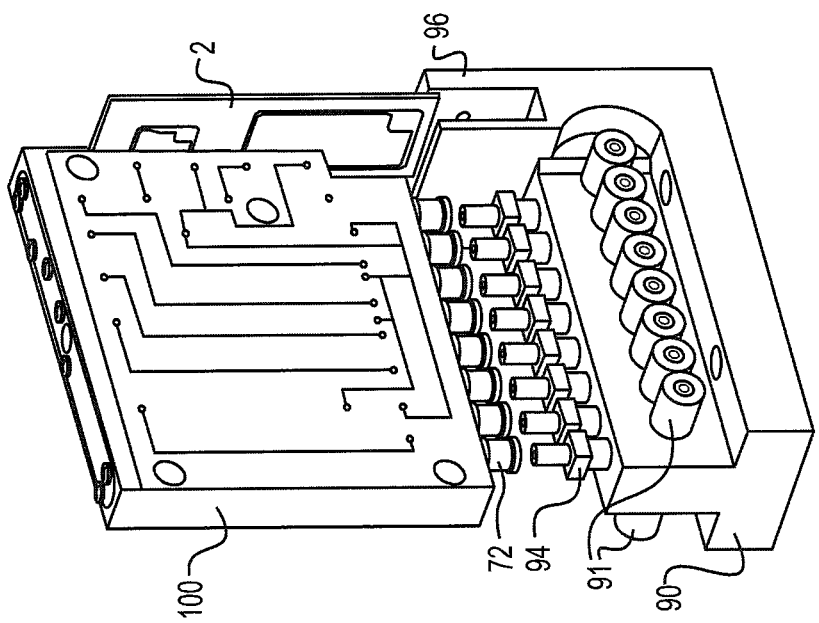
FIG. 6A is a schematic showing an integrated cartridge residing in a fluidic manifold without the thermocycler bladders.

FIG. 6A shows an embodiment of a fluidic manifold 90. In this embodiment, the manifold 90 allows two fluidic fittings 91 to be connected for each cartridge port 72. The manifold has eight bosses 94 with luer tapers. These bosses have a fluidic channel that provides a flow path from the fluidic fittings to the cartridge port. In this embodiment, the fluidic manifold 90 contains a holder 96 that is configured to hold a pair of thermocycler bladders, such as those described in U.S. patent application Ser. Nos. 11/843,843 and 12/232,669, in such a manner so that the amplification chamber 5 of the sample analysis unit 2 of the integrated cartridge 100 is positioned between the two thermocycler bladders 92 when the integrated cartridge 100 resides on the fluidic manifold 90. FIG. 6B shows a fluidic manifold 90 with the integrated cartridge 100 and the thermocycler bladders 92.

Figure 8:
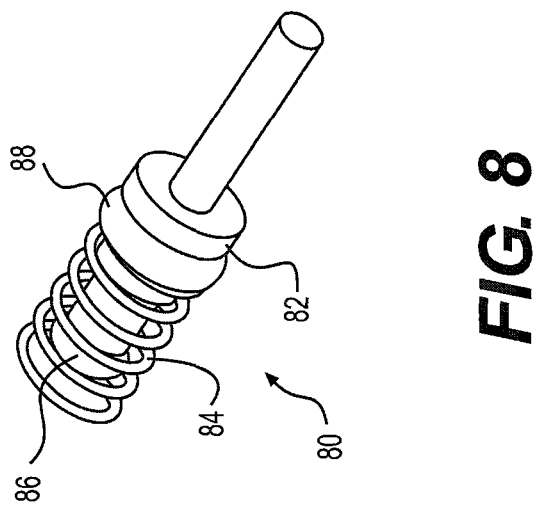
FIG. 8 is a schematic showing an embodiment of an on-board microfluidic cartridge valve.
Figure 7:
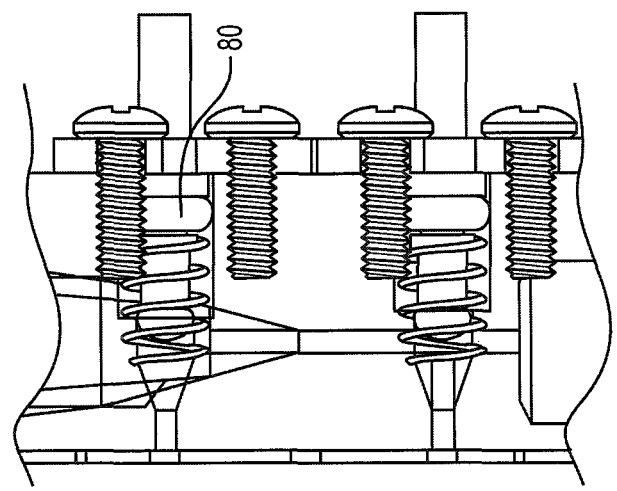
FIG. 7 is a schematic showing the location of the on-board microfluidic cartridge valves in an integrated cartridge.

Liquid flow within the integrated cartridge 100 is also controlled by on-board cartridge valves 80. FIG. 7 shows the location of the on-board microfluidic cartridge valves 80 in an embodiment of integrated cartridge 100. FIG. 8 shows an embodiment of a valve 80. In this embodiment, the valve 80 is made of a machined plastic body 82, a spring 84, an inner o-ring 86 and an outer o-ring 88, and are screwed in place. The machined parts can also be injection molded to reduce cost. In another embodiment, the valves further contain a valve alignment fixture (not shown) for rapid and consistent insertion on the cartridge. The valves can be secured on the cartridge by laser welding, heat staking, ultrasonic welding or snap fitting in lieu of being screwed in place.

The on-board valves 80 may be opened and closed by manually turning screws to push the valve shaft in and out. Alternatively, an automated linear actuator panel with supporting electronics and software may be implemented to control the on-board cartridge valves electronically based on the required protocol.

In one embodiment, the fluidic subsystem includes two bidirectional pumps: one for sample preparation and one for polymerase chain reaction (PCR) and/or APEX. These pumps connect to a carrier solution and the center of a selection valve. The pumps have two types of holding coils associated with them: a circular coil to provide mixing by the "racetrack" effect and a switchback coil that alternates between streamlines that undergo the racetrack effect.

In this embodiment, the fluidic subsystem contains three 10-port selection valves to provide flexibility and to isolate sample preparation from the PCR/APEX fluidics. One of the selection valves serves to aliquot sample preparation reagents to the cartridge with an embedded Akonni TruTip, another serves to aliquot PCR and APEX pellet rehydration buffers to the cartridge, and the third serves as a means of venting or applying positive pressure to reservoirs on the cartridge. Increasing the number of ports per selection valve is one way to increase the number of cartridges per instrument without adding hardware complexity.

The cartridge pin valves serve two purposes: (1) they allow a single reagent supply line to serve multiple reservoirs on the cartridge and (2) they control liquid movement that would otherwise be directed in unwanted pathways due to the compliance of air. Miniature linear actuators open and close the cartridge pin valves with forces less than 35N.

Small holders were designed and implemented to rigidly position the actuators concentric with the shaft of the pin valves. The holder design allows the actuator to be rotated along the axis of the pin valve shaft to tightly pack multiple actuators into place. This design is necessary because the body of the actuator protrudes from the axis, giving it a quasi-elliptical profile (i.e., the actuators are not axisymmetric). The actuators are secured to an I-Beam to rigidly secure them to the instrument. The arm of the actuators penetrate through holes on a second I-Beam, which provides support for the cartridge. This second I-Beam has a linear pattern of threaded holes that allow standoffs to be fastened to it. The standoff also has a threaded hole that accepts a bolt, which penetrates through the cartridge. The bolts keep the cartridge in a fixed position with respect to x, y and z dimensions. In one embodiment, the pin valves are secured by screws. In another embodiment, multiple pin valves are being actuated by a single actuator.

B. The Bladder Thermocycler Subsystem

The bladder thermocycler subsystem is described in U.S. patent application Ser. Nos. 11/843,843 and 12/232,669, both of which are incorporated herein by reference in their entirety.

In one embodiment, the bladder thermocycler subsystem consists of 2 pumps, 3 three-way valves, three heaters (two for the denaturing flow loop and one for the annealing/extension flow loop), 2 reservoirs that serve as bubble traps and refilling access, a radiator, and a bladder assembly having two flexible bladders facing each other. In this embodiment, the pump is a diaphragm pump with a flow rate range of 0.15-2.00 liters per min, and operates up to 82° C. To protect the temperature of the pump from the heaters, a PVC fitting was used to insulate the heater from the pump.

Figure 9:
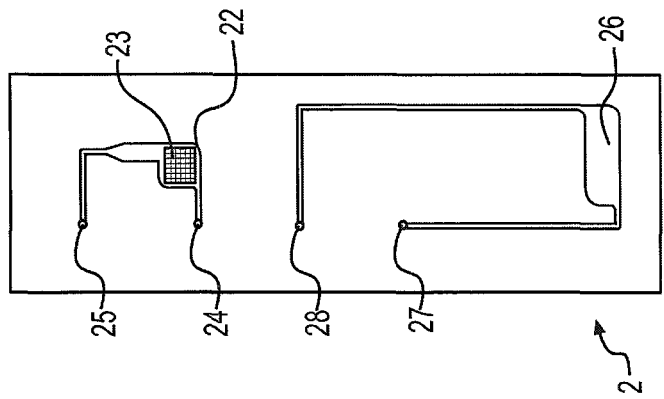
FIG. 9 is a schematic showing an embodiment of the chamber arrangement within a flow cell.
Figure 10:
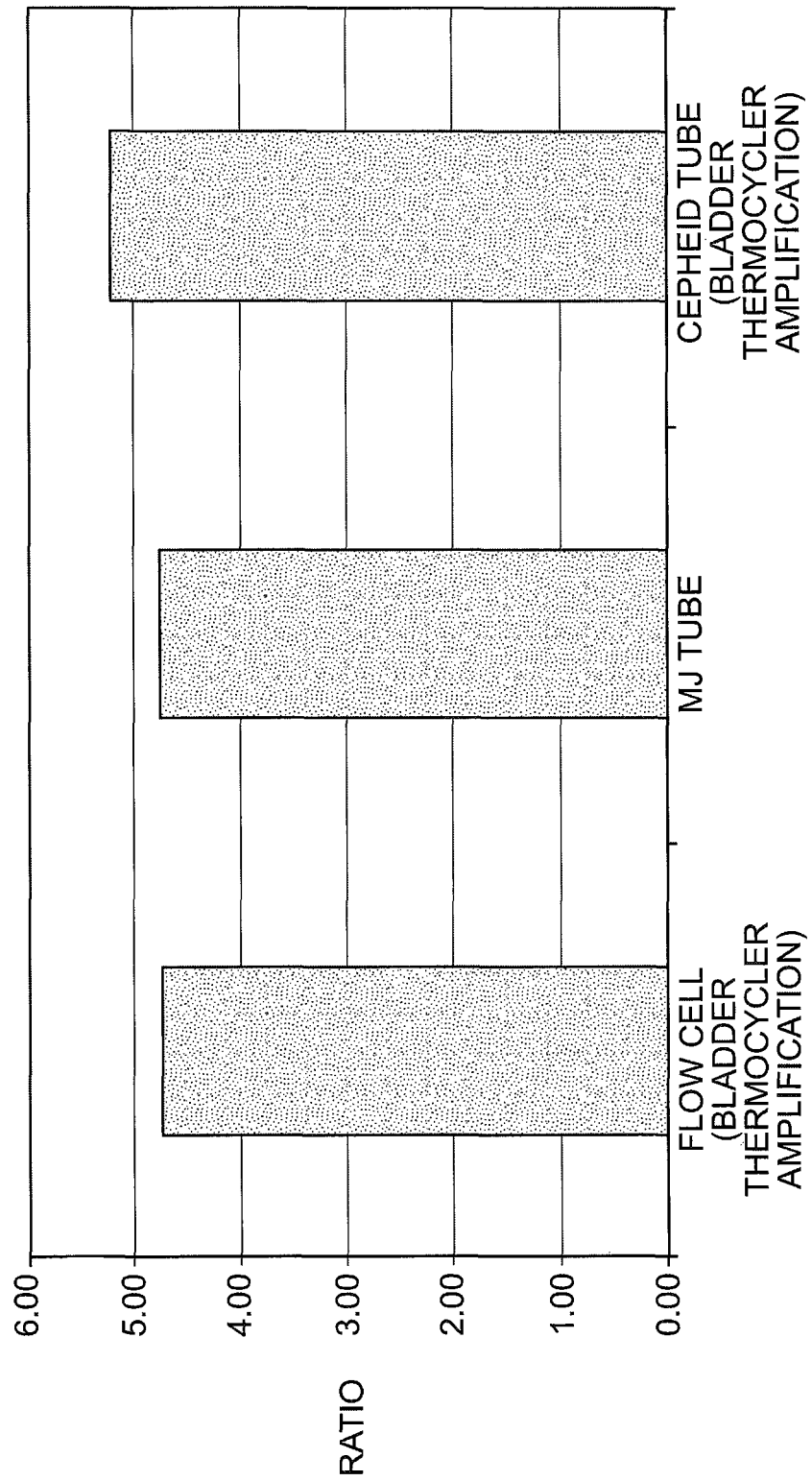
FIG. 10 is a diagram showing PCR/APEX allele signal ratio results obtained for an eye color SNP at position RS1800407. PCR was performed in a Akonni flow cell positioned in a bladder thermocycler, in 0.2 ml PCR tube positioned in a MJ thermal cycler, and in Cepheid tube positioned in the bladder thermocycler. APEX was performed offline for one hour. The results indicate comparable APEX signals for all three PCR approaches.

The ramp times with this system are approximately 10° C./sec for both heating and cooling. For preliminary evaluation of performance for this iteration of the bladder thermocycler, a PCR reaction was performed in a Cepheid Smart Cycler tube (flat reaction tube) inserted between the bladders in the bladder assembly of the bladder thermocycler and in a standard 0.2 ml PCR tube inserted in an MJ Research thermocycler. Both thermocyclers generated equivalent levels of product. FIG. 9 shows an embodiment of a detachable sample analysis unit 2. In this embodiment, the detachable sample analysis unit 2 is a flow cell having an array chamber 22 with a microarray 23, an inlet port 24 and an outlet port 25, and a PCR chamber 26 with an inlet port 27 and an outlet port 28. As shown in FIG. 6B, the flow cell is attached to one side of the integrated cartridge so that the PCR chamber is extended from the side of the integrated cartridge into the bladder heating units of the thermocycler which is attached to the fluidic manifold. FIG. 10 demonstrates PCR in a flow cell and subsequent APEX using the bladder thermocycler, showing equivalent discrimination in both a tube-based format and a Cepheid Smart Cycler tube on the bladder thermocycler.

In one embodiment, the MSTA system is designed for room temperature hybridizations. In another embodiment, the MSTA system comprises an isothermal heating system for heating the array chamber. The isothermal control can be achieved by blowing heated air at the back side of the array chamber with a thermocouple at the nozzle of the air flow tube. In certain embodiments, the isothermal heating system is capable of maintaining the temperature of the array chamber in the ranges of 20° C.-65° C., 20° C.-75° C., 20° C.-85° C. or 20° C.-95° C.

C. The Optical Subsystem

Figure 11A:
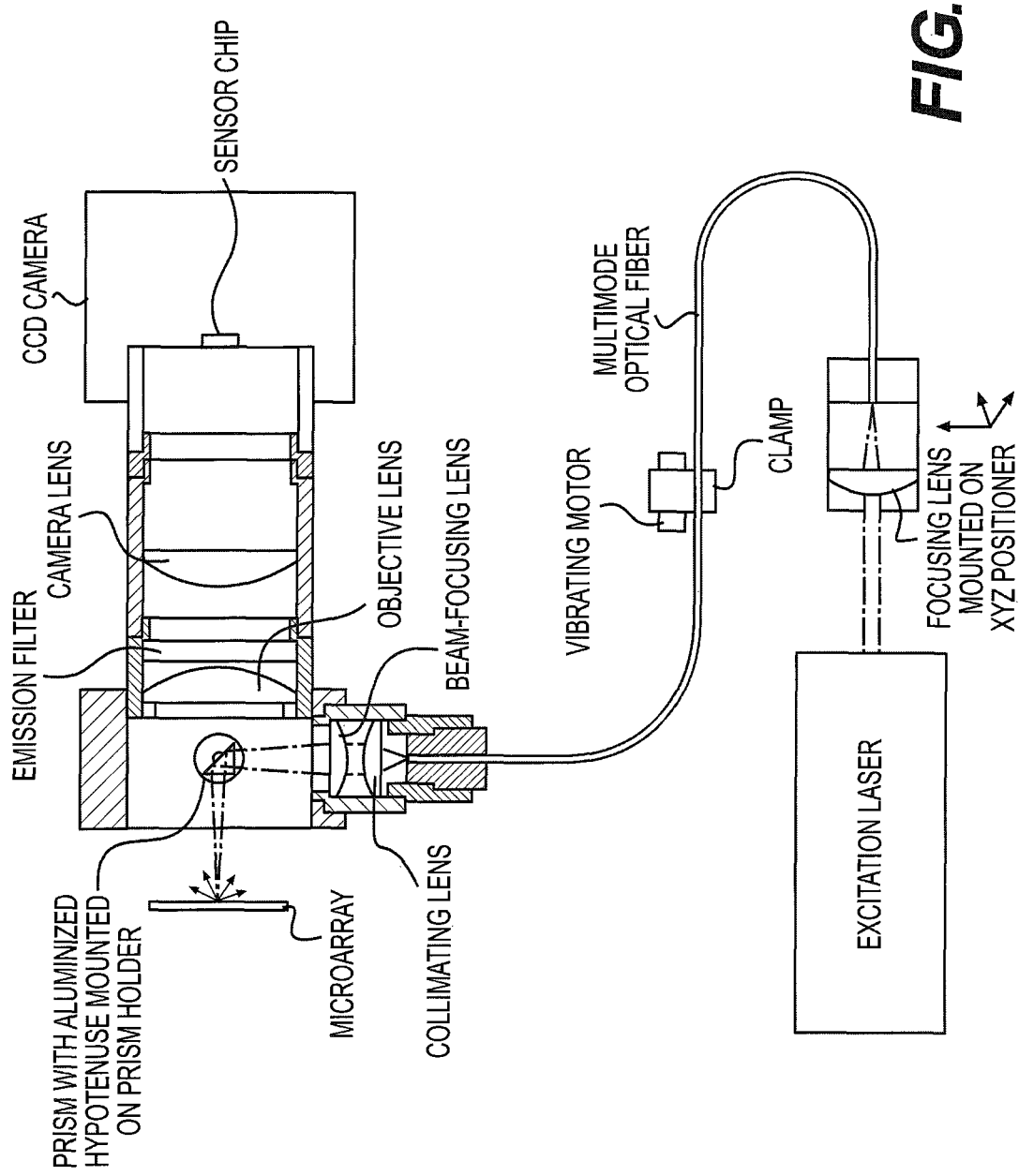
FIG. 11A is a schematic of an embodiment of the optical subsystem with a laser light source.

FIG. 11A is a schematic of an embodiment of an optical subsystem. The low-cost optical subsystem is developed for reading arrays of a relatively low complexity (number of array elements <50). The CCD camera used in this subsystem of the reader is a miniature non-cooled camera of ⅓" optical format with resolution 659×493 pxl and a pixel size of 7.4×7.4 µm (e.g. a Prosilica model EC650).

Both the objective and camera lenses are identical F/1.5 single-element aspheric lenses such as Edmund Optics part #NT47-732. The lenses have an effective focal length of 37.5 mm. Since the magnification of the imaging system is equal to 1, the pixel size in the object plane is the same as the pixel size of the CCD sensor (7.4 µm).

The useful field of view (FOV) is about 2 mm in diameter, which is enough for imaging arrays comprising up to 50 spots under assumption that the array pitch is 300 µm. The FOV-limiting factor is the field curvature, which predictably is relatively high for this simplistic optical setup.

Another distinctive feature of the optical design (in addition to the objective lens with high light-collection efficiency ensured by the low f-number of 1.5) is the co-axial illumination scheme that employs a 15 mW green (532 nm) DPSS laser and a multimode optical fiber that is used not only for beam delivery, but also for beam shaping and speckle suppression.

Because of the multimode nature of the fiber, the Gaussian intensity distribution in the laser beam at the fiber input face is transformed into a top-hat-like distribution at the fiber output. The collimating and beam-focusing lenses work together to project the image of the fiber end face onto the object plane of the objective lens. As a result, the intensity distribution in the object plane is similar to that at the fiber output, whereas the size of the illuminated spot is determined by the fiber core diameter and the magnification factor of the two-lens projection system.

The speckle suppression is achieved with the help of a miniature vibrating motor attached to the fiber (see FIG. 11A). Vibrating the fiber results in rapid modulation of the phase shifts between different fiber modes, which translates into high-frequency intensity oscillations in the speckle pattern. The latter are effectively smoothed out in the process of taking the image even for exposures as short as 100 ms.

In one embodiment, a low-cost optical subsystem scans a microarray and stitches the images together to generate a complete picture of the microarray. In another embodiment, arrays on multiple cartridges are consecutively scanned using a linear motion system.

Figure 11B:
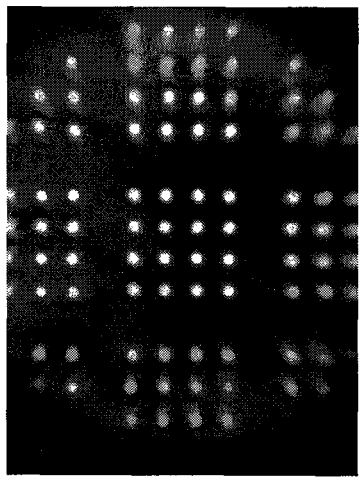
FIG. 11B shows a typical image of a Cy3 array with a pitch of 300 nm taken with the optical subsystem described in FIG. 11A with the co-axial illumination.

FIG. 11B shows a typical image of a Cy3 array with a pitch of 300 µm taken with the optical subsystem described in FIG. 11A with the co-axial illumination.

Figure 12A:
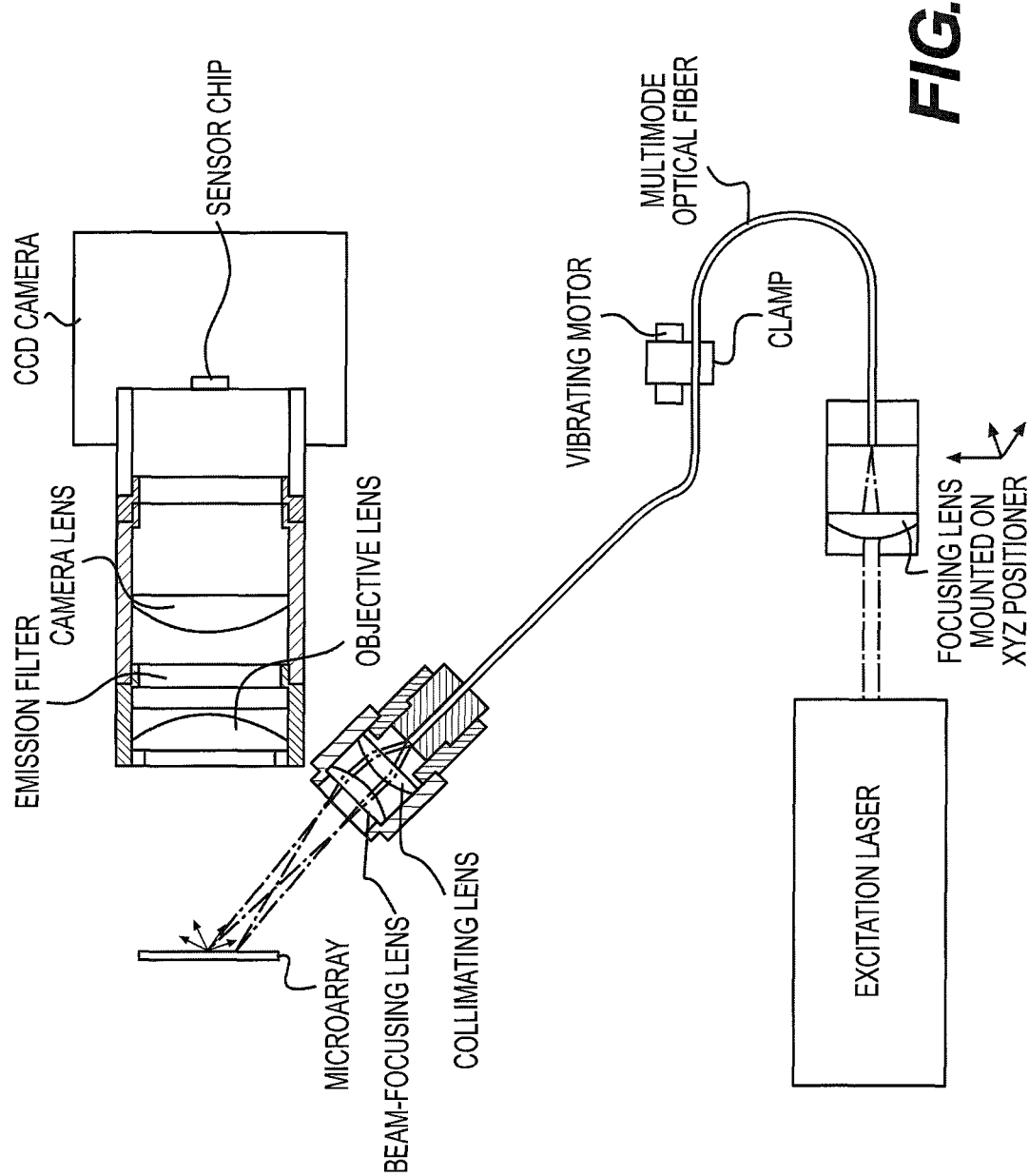
FIG. 12A schematic of another embodiment of the optical subsystem with a laser light source.

FIG. 12A is a diagram of another optical subsystem. This version of optical subsystem was developed for imaging arrays with the number of features up to 200, which is sufficient for many diagnostic assays. Expanding the field of view calls for the objective lens with a high degree of aberration correction. It also makes it necessary to use a lens with a higher f-number. An example of an objective that satisfies the above requirements is a Leica's infinity-corrected Planapo 2× lens with a working distance of 39 mm and a numerical aperture of 0.234. It should be noted that the objective and camera lenses in the imaging optical path of the optical subsystem are shown as single-element lenses for the sake of simplicity only. In fact, both these lenses are highly corrected multi-element optics that work at infinity conjugates and have the focal length equal to each other. So the magnification factor of the entire lens system is 1.

Figure 12B:
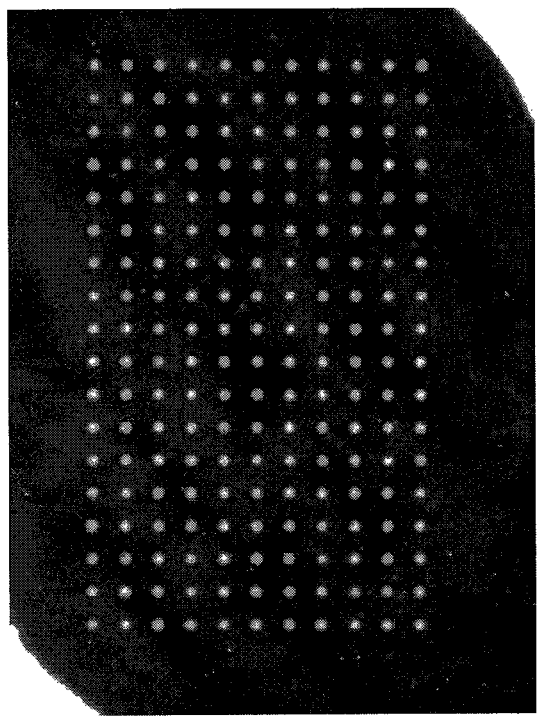
FIG. 12B shows a typical image of am 11×18 Cy3 array taken with the optical subsystem of FIG. 12A.

In another embodiment, the focal length of the beam-focusing lens was increased to expand the illuminated spot in the object plane to about 8 mm It was found experimentally that with the spot diameter that large, the non-uniformity of illumination caused by the oblique angle of beam incidence did not exceed 5%. FIG. 12B represents a typical image of a m 11×18 Cy3 array taken with the optical subsystem employing the oblique illumination scheme (FIG. 12A). As described above, the array pitch is 300 μm, and a characteristic diameter of the array spots is about 120 μm.

FIG. 13A shows another embodiment of the optical subsystem. In this embodiment, the laser in the oblique illumination design is replaced with a high-brightness light-emitting diode (LED). The LED illuminator shown implements a Köhler illumination scheme (A. V. Arecchi, T. Messadi, and R. J. Koshel, Field Guide to Illumination, SPIE Press Book, Vol. FG11, Aug. 31, 2007, ISBN: 9780819467683, which is incorporated herein by reference) for projection systems and includes a clean-up filter placed between the collector and condenser lenses and a beam-steering mirror directing the excitation light at the object plane at oblique angle. The filter is intended for rejecting the spectral components of LED light overlapping with the emission spectrum of the dye used for DNA labeling (e.g. Cy3). Although the embodiment shown in FIG. 13A is a preferred one, it will be apparent to those skilled in the art that the beam delivery system with a mirror may be modified without departing from the scope and spirit of the invention. In particular, a liquid light guide or fiber optic bundle could be introduced in the optical train to facilitate beam delivery from a remote light source.

Figure 13C:
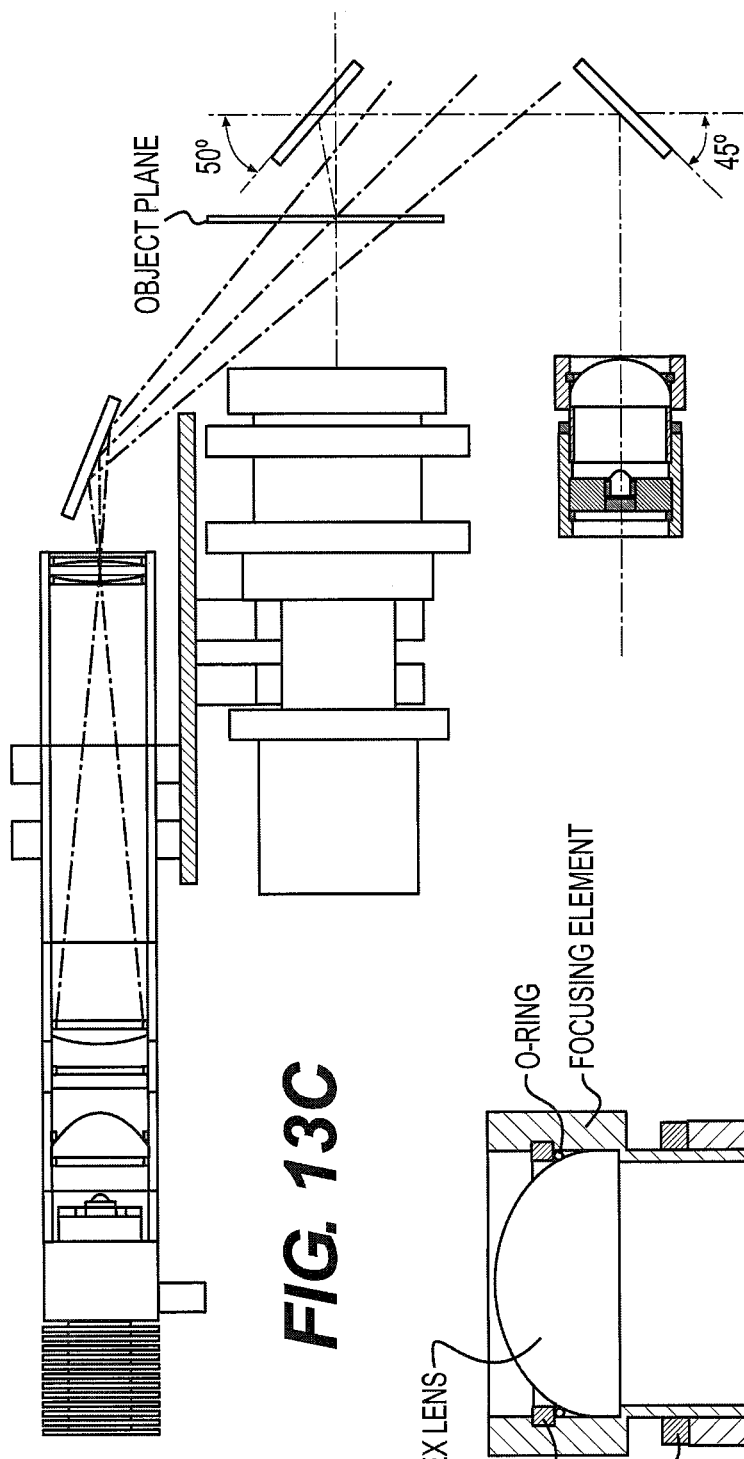
FIG. 13C is a schematic showing another optical train for fluorescence and FII imaging.
Figure 13D:
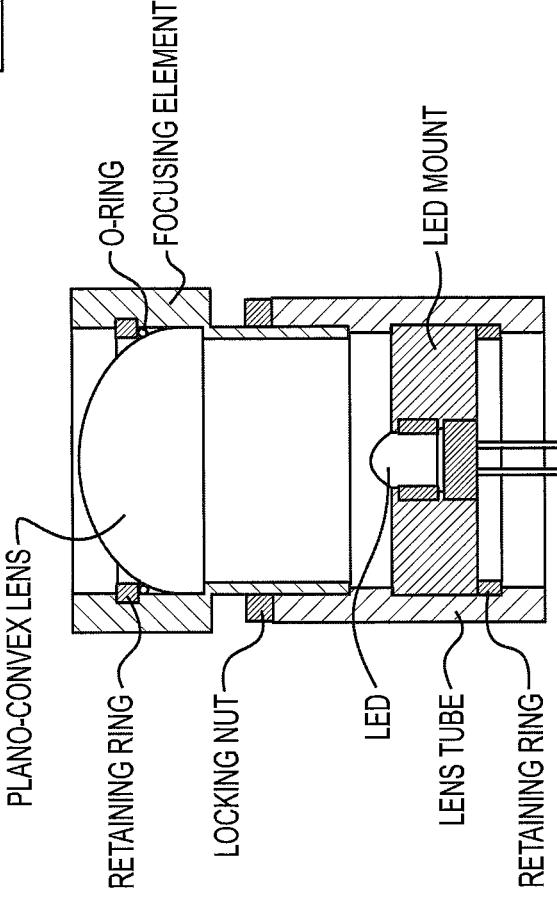
FIG. 13D is a schematic showing a collimated source used in FIGS. 13B and 13C.

In other embodiments, the optical subsystem comprises a miniature low-power LED for FII. FIG. 13B shows an embodiment of an optical train capable of both the fluorescence imaging and FII using oblique illumination in transmitted light. FIG. 13C shows an embodiment of an optical train capable of both the fluorescence imaging and FII using darkfield illumination in reflected light. The optical train in FIG. 13C requires less space behind the slide holder (i.e., the object plane). FIG. 13D shows an exemplary technical implementation of a collimated source. The light emitter used is a low-intensity yellow LED with a peak emission wavelength of 591 nm.

Figure 14B:
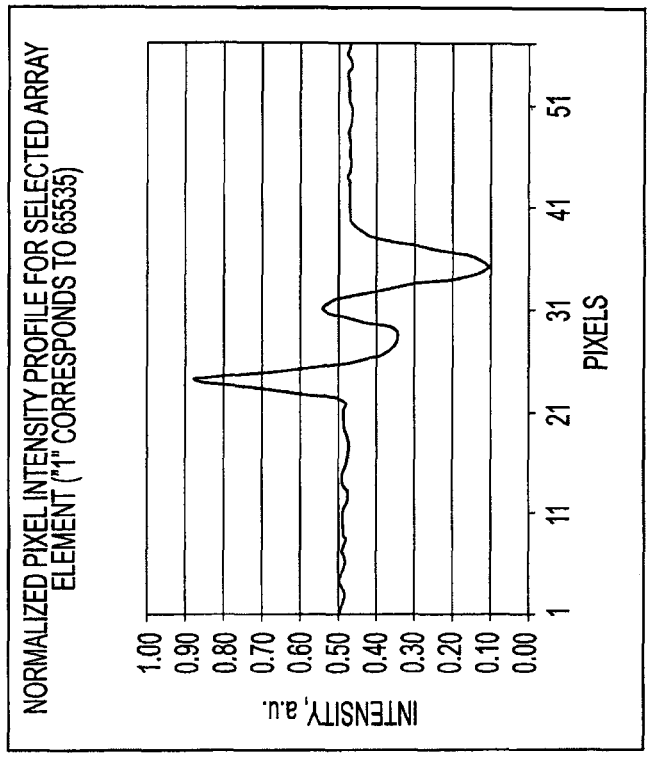
FIG. 14B is a diagram showing the normalized pixel intensity profile of an array element in FIG. 14A.
Figure 14A:
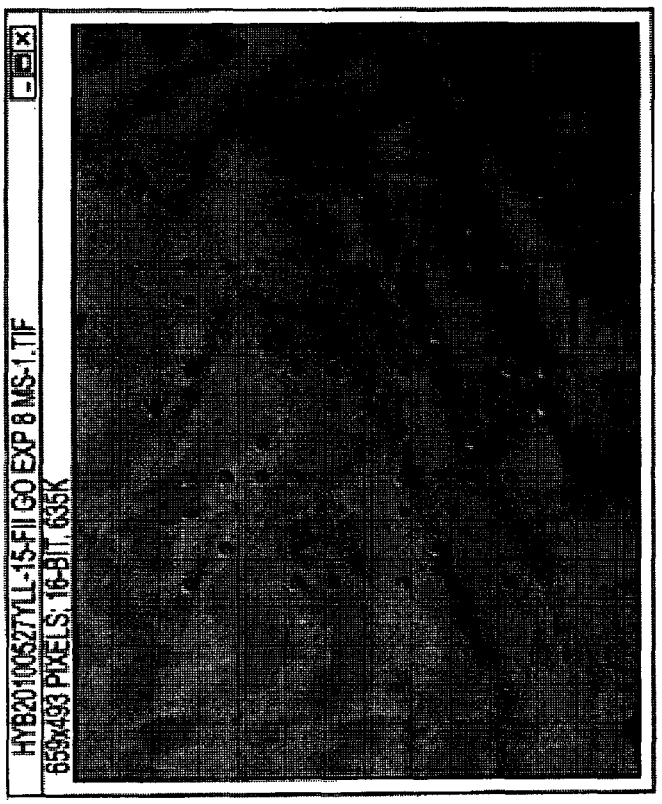
FIG. 14A is an FII image of a gel array.
Figure 15B:
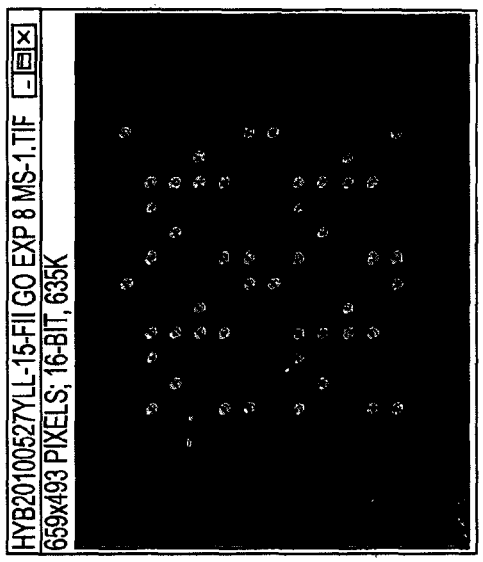
FIG. 15 is a composite of images showing a gel array image processed by different methods available in the ImageJ software. Panel A, original image; Panel B, ImageJ processing: Process=>Find Edges; Panel C, ImageJ processing: Process=>Filters=>Median, R=5; Panel D, ImageJ processing: Process=>Filters=>Mean, R=5; Panel E, ImageJ processing: Image=>Adjust Threshold; Panel F, ImageJ processing: Process=>Filters=>Maximum . . . R=2; Panel G, ImageJ processing: Process=>Binary=>Find Maxima; Panel H, Superposition of the images showing respectively spot centers found and spot boundaries detected.
Figure 15D:
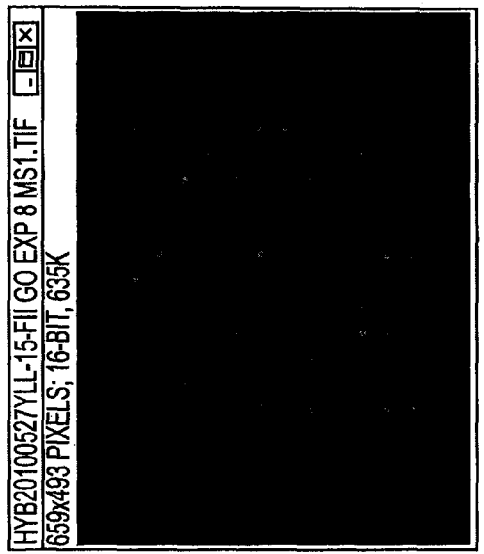
Figure 15A:
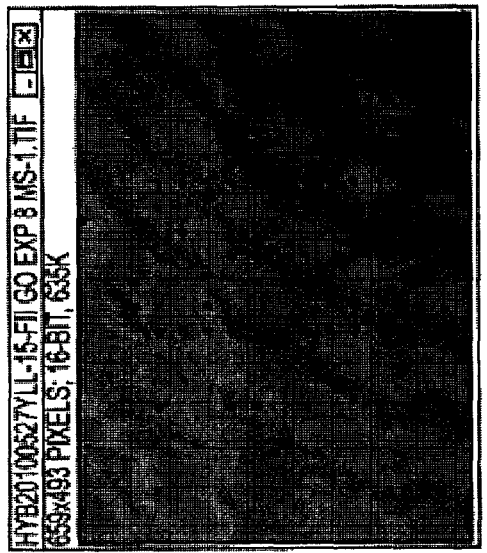
Figure 15C:
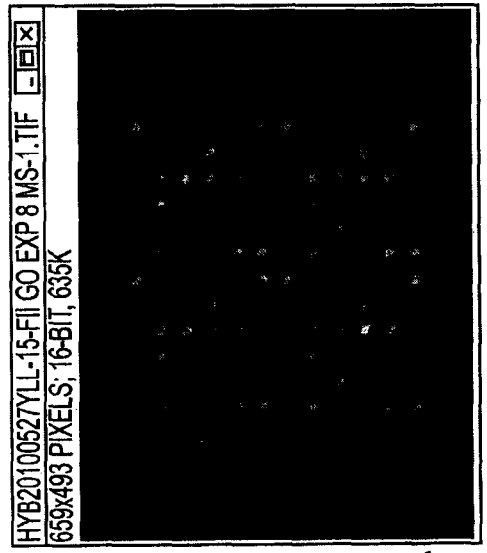
Figure 15E:
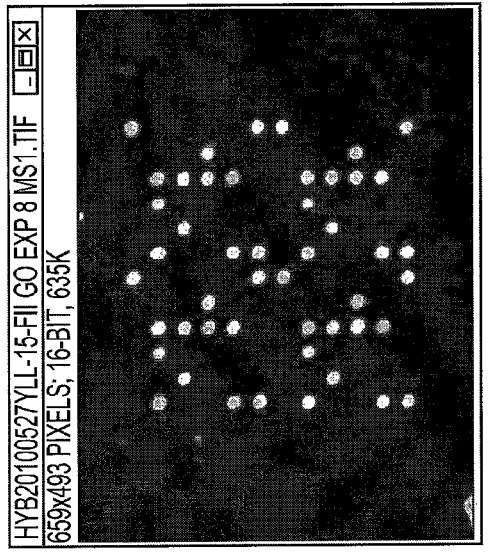
Figure 15F:
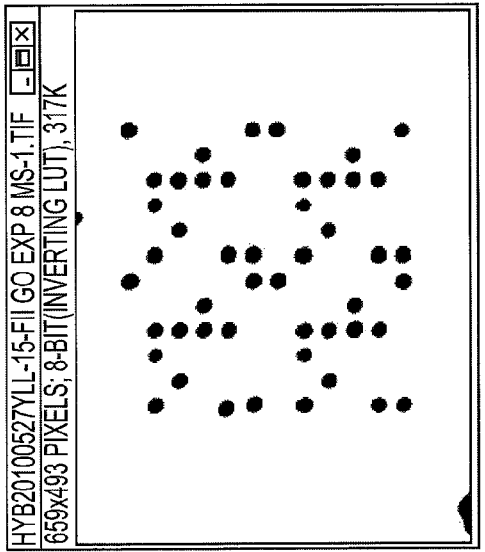
Figure 15G:
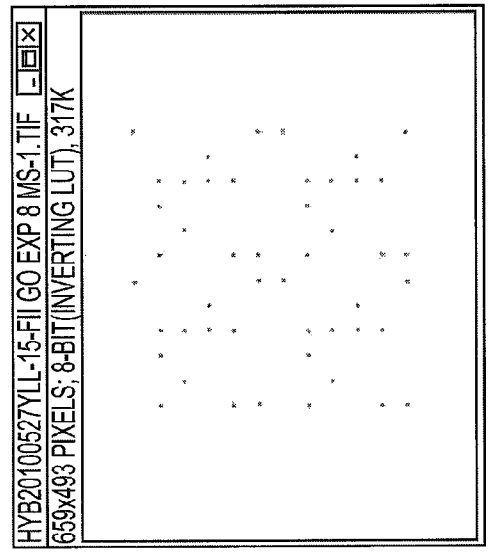
Figure 15H:
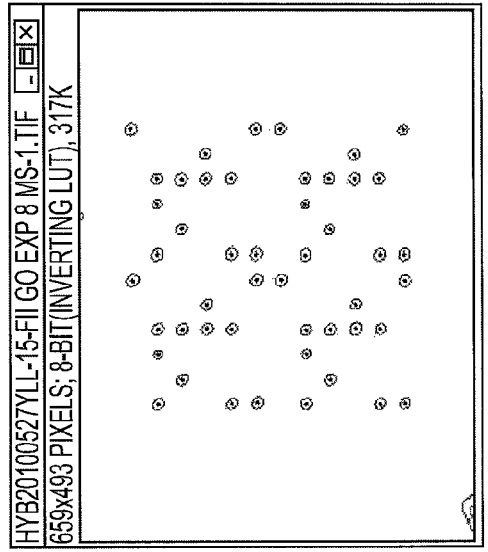
Figure 16B:
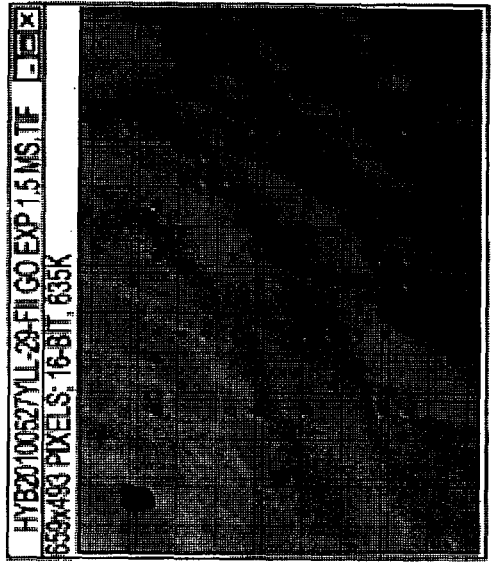
FIG. 16 is a composite showing evaluation of spot morphology. Panel A: image obtained in the fluorescence imaging mode; Panel B: FII image of the same array obtained using oblique illumination with collimated beam; Panel C: Image processing in ImageJ using Process=>Find Edges; Panel D: Image processing in ImageJ using Process=>Filters=>Median, R=2; Image=>Adjust threshold.
Figure 16D:
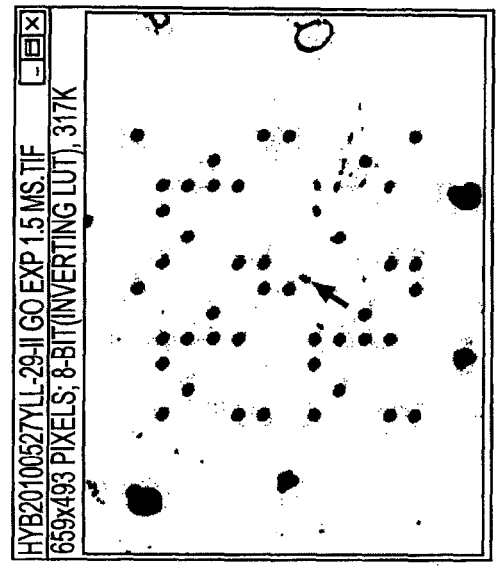
Figure 16A:
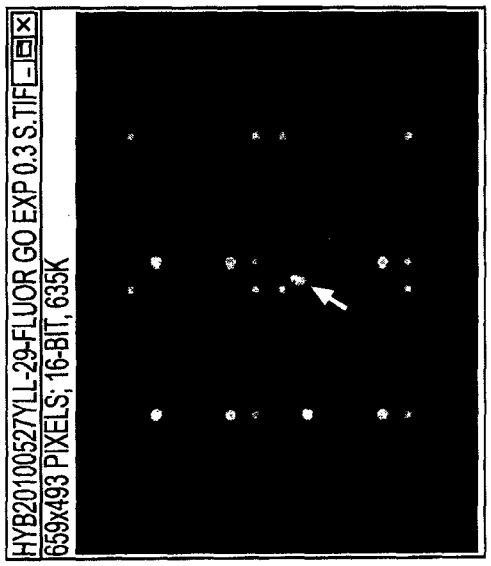
Figure 16C:
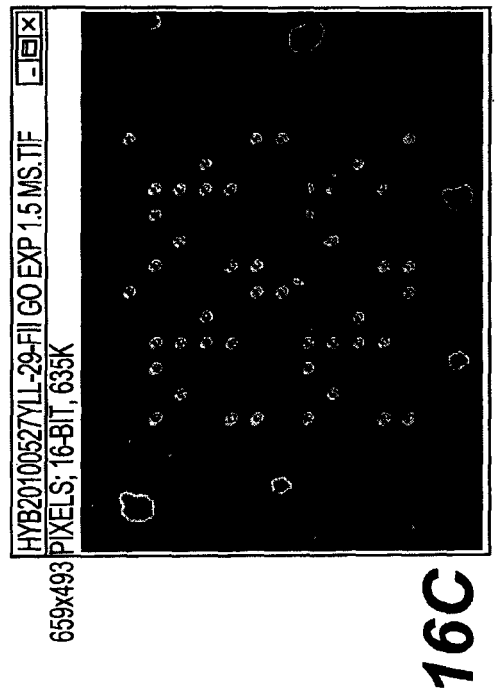

FIG. 14A shows an exemplary image of Akonni MRSA assay slide recorded using oblique illumination with a collimated beam of LED light source. FIG. 14B shows the normalized pixel intensity profile of an array element in FIG. 14A. Although images with the highest contrast were typically obtained using oblique illumination with a collimated light source, other optical arrangements for oblique illumination are also possible. The general requirement for such schemes is asymmetrical distribution of illumination intensity between different azimuths. The FII array image can be processed for the purposes of gridding and spot morphology analysis using relatively simple image processing tools, such as the image processing tools in the ImageJ software (http://rsbweb.nih.gov/ij/). FIG. 15 is a composite of images showing a gel array image processed by different methods available in the ImageJ software. FIG. 16 is a composite showing evaluation of spot morphology using the ImageJ software.

Figure 17A:
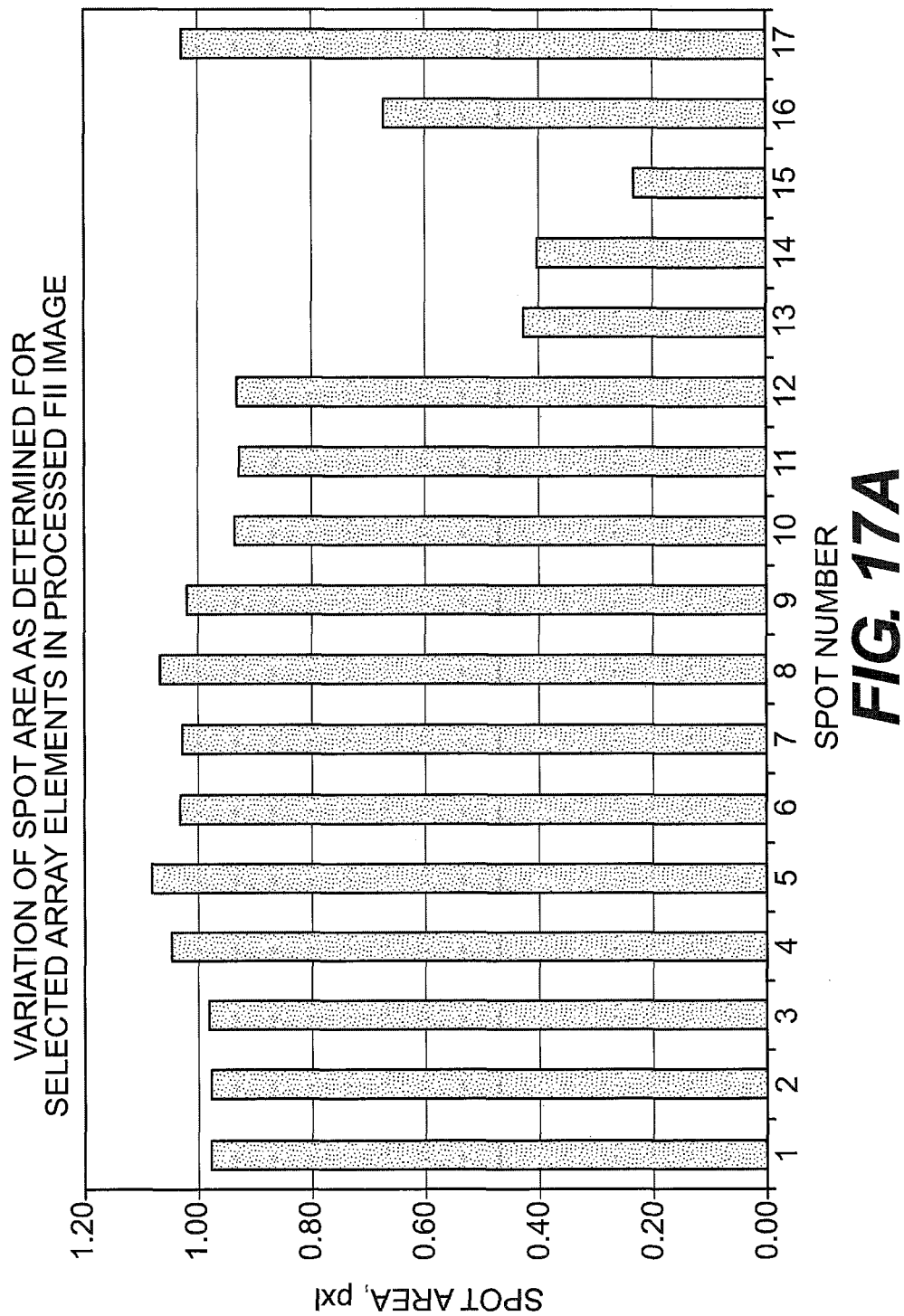

FIGS. 17A and 17B are graphs showing evaluation of morphology for the gel spots in panel A of FIG. 15. In this study, FII imaging using oblique illumination with a collimated beam allowed both detection of array spot centers and identification of damaged spots with considerable morphology abnormalities. The data suggest that, for the best sensitivity of morphology analysis, the spots need to be characterized by a combination of parameters. For example, by spot area and parameters of best fitting ellipse;

It should be noted, however, that array image QC cannot rely solely on the FII imaging mode: some of the image features that may seem innocuous in an FII image can, in fact, be a source of considerable interference for spot fluorescence intensity measurements (e.g., the particle marked by the arrow in panels A and D of FIG. 16).

Example 2

Detection of Bacteria in Test Samples with Integrated Cartridge and the Microarray Based Sample Analysis System The sequence of events for the MBSA system are as follows. The user introduces a sample into the integrated cartridge. The system then performs the following automated steps: prepare the samples, perform PCR using a Bladder Thermocycler™, mix the PCR product with a hybridization and/or APEX reaction mixture, transfer the mixture to the microarray chamber, perform hybridization to the microarray, and detect the microarray image.

In one embodiment, the sequence of steps for preparing samples on the cartridge are: introduce the sample into the sample tower, introduce the bind buffer into the sample tower, mix with air, transport the sample mix to the TruTip tower, toggle between the towers, dispense to waste, introduce the wash buffer to the TruTip tower, toggle between the towers, dispense to waste, introduce the elution buffer, and dispense to the elution tower.

The sequence of steps for PCR are: add PCR mix to the elution tower or reconstitute a lyophilized reagent pellet with elution buffer following sample processing, dispense to PCR chamber on flow cell, close all cartridge pin valves, and start thermocycling.

The sequence of steps for APEX are: flush PCR chamber with APEX buffer and add to APEX reservoir, thoroughly mix, add APEX reagent to array chamber, incubate at 65° C., wash, and image.

In one experiment, 500 μL of $10^5$ cfu/mL of *Streptococcus pyogenes*, which had been lysed offline by vortexing for 2 minutes, was introduced into the sample chamber of an integrated cartridge. The cartridge was connected to a prototype MBSA system comprising a cartridge adaptor, a fluidic control subsystem for sample preparation and processing, a thermal control subsystem for PCR amplification, an optical subsystem and a data acquisition board and PC for image acquisition.

The following steps are controlled by the analytical system. Bind buffer was added to the sample mixing chamber, and mixed with the sample by air bubbles that migrate from the bottom of the chamber to the top of the chamber. The air bubbles were controlled by regulated air flow from the instrument pump. The mixed sample was then introduced into the sample purification chamber, which contains the silica extraction filter that binds specifically to DNA, and cycled 5 times back and forth across the matrix to improve binding efficiency. The unbound material was then directed to the waste chamber in the cartridge by means of on-board cartridge valves. Leaving the waste in the cartridge prevents contamination with subsequent samples. A wash buffer was subsequently toggled 5 times between the TruTip tower and the sample preparation tower and then directed to the waste chamber. One hundred and twenty microliters of elution volume was then introduced from the analytical system onto the cartridge through the TruTip tower and then directed into the elution chamber, which removes the bubbles.

A 10 ul aliquot of the eluted DNA was removed and processed on a Roche 480 real-time PCR Light Cycler. A second aliquot of the eluted DNA was also removed from the elution chamber and amplified "off-line" in a representative flow cell. A PCR master mix is then introduced into the elution chamber. The eluted sample was mixed with the master mix by bubbling air from the bottom of the elution chamber. The mixed sample was then directed, via on-board valves into the PCR chamber of a flow cell attached to the integrated cartridge, which was positioned between two compliant bladders of the thermocycler when the cartridge is inserted in the fluidic docking station. A manufacturing benefit to the use of compliant bladders is that because they expand and make intimate contact with the cartridge flow cell, they can accommodate a large range of flow cell thicknesses and positional variations without changing the design. Forty cycles of two-temperature PCR was performed by oscillating two temperature fluids through the bladder using the Bladder Thermocycler™ method. This method is based on flowing heated liquids into a flexible membrane ("bladder") that makes intimate contact with the PCR chamber. Valves switch between thermally-controlled reservoirs to provide a rapid change in temperature. This thermocycling approach results in PCR protocols that are approximately 4× faster than conventional slide thermocyclers, which rely on Peltiers for heating and cooling.

Figure 18B:
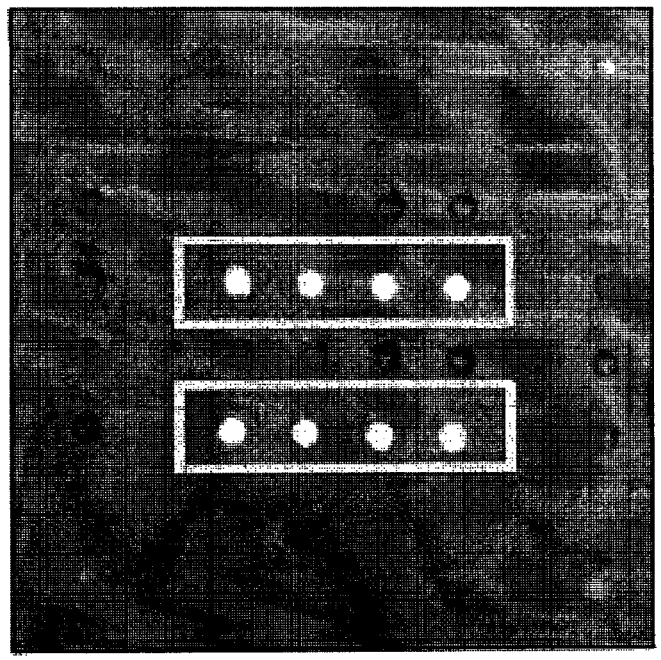
FIG. 18B is picture showing detection of *S. pyogenes* with a prototype MBSA system and an Akonni imager.
Figure 18A:
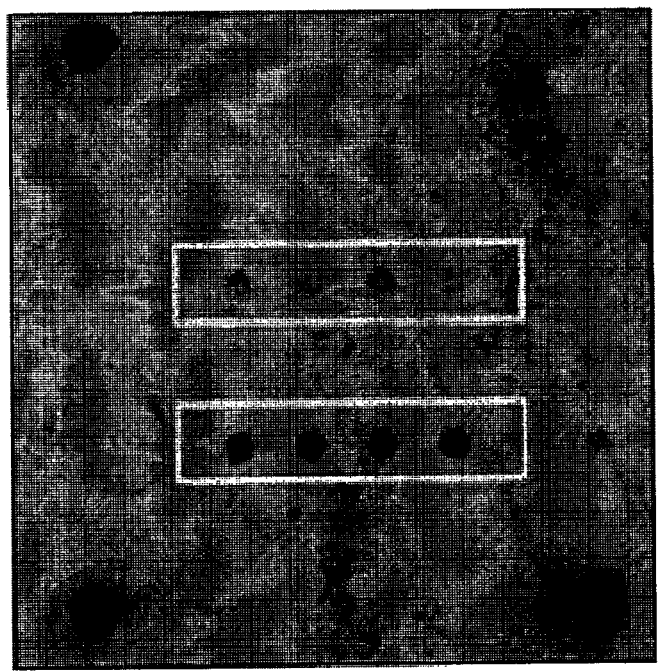
FIG. 18A is picture showing detection of *S. pyogenes* with a prototype MBSA system and an Aurora imager.
Figure 19B:
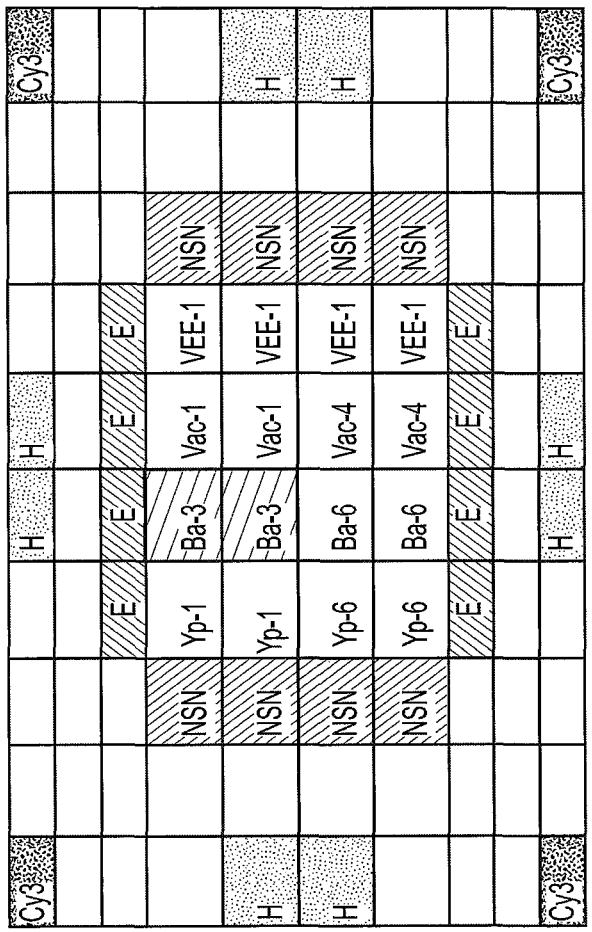
FIG. 19B is an array map of the microarray used in FIG. 19A.
Figure 19A:
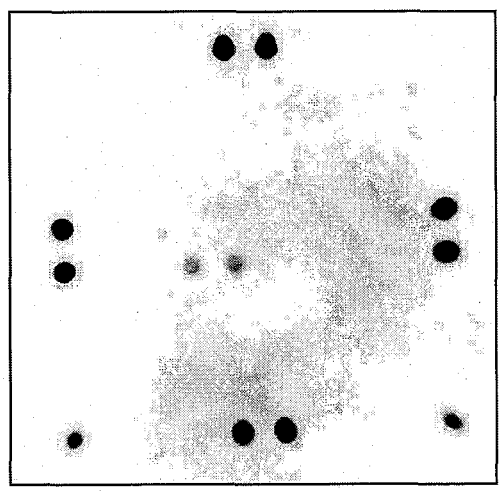
FIG. 19A is a picture showing detection of *B. anthracis* with a prototype MBSA system and the imaging approach shown in FIG. 11A.
Figure 20:
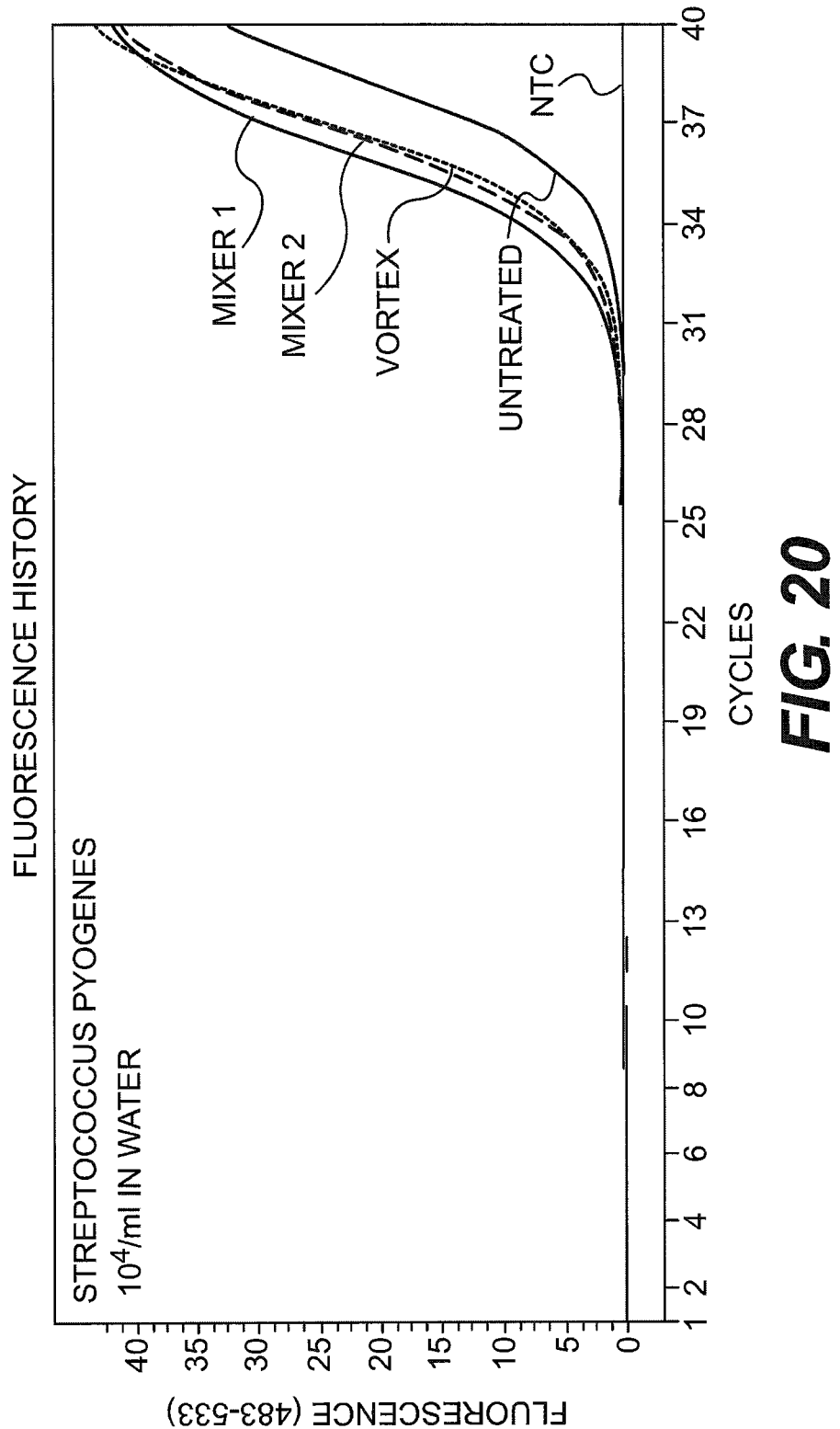
FIG. 20 is diagram showing PCR results of S. pyogenes DNA extracted using an integrated cartridge with a bead mixer. Mixer 1 and mixer 2: S. pyogenes DNA extracted in two separated experiment using an integrated cartridge with a bead mixer. Vortex: S. pyogenes DNA extracted using standard vortexing method. NTC: negative control.

Following amplification, the PCR product was automatically transferred to the microarray chamber of the flow cell through the on-board cartridge valves and hybridized to the microarray in the microarray chamber for one hour at room temperature. The microarray was then read with an Aurora PortArray 5000 imager. FIG. 18A shows an image of the hybridized microarray taken from the Aurora Port Array 5000. The positive signals are indicated by the boxes.

The second aliquot of the eluted DNA was amplified "off-line" in a flow cell identical to the flow cell attached to the integrated cartridge. Briefly, the DNA sample was manually loaded into the PCR chamber of the flow cell and amplified as described above. The amplification product was then manually loaded into the microarray chamber and hybridized to the microarray in the microarray chamber for one hour at room temperature. The microarray was then read with an Akonni imager specifically designed for gel element arrays and flow cell assemblies. FIG. 18B shows an image of the hybridized microarray taken from the Akonni imager. The positive signals are indicated by the boxes.

In another experiment, 500 μl *Bacillus anthracis* sample ($10^4$ cfu/ml in water), was processed and analyzed using the procedure described above. FIG. 19A shows an image of the microarray that indicates positive detection of *Bacillus anthracis* in the test sample. FIG. 19B is the array map for the microarray used in FIG. 19A.

In another experiment, 500 μl *Streptococcus pyogenes* sample ($10^4$ cfu/ml in water) was processed using an integrated cartridge with a magnetic bead mixer in the sample preparation chamber. Glass beads were added to the chamber and the bead mixer was agitated to lyse the organism in the chamber. FIG. 20 shows PCR results of DNA extracted with the mixer. The vortexing method was accomplished by mixing beads to sample volume at a ratio of 50/50 and vortexed for 2 minutes in a 1.5 mL micro centrifuge tube.

Example 3

Genotyping of Single-Nucleotide Polymorphism (SNP Typing) with Integrated Cartridge and the Microarray Based Sample Analysis System This example demonstrates the feasibility of a microfluidic-controlled system for SNP-typing of physical appearance markers that could be utilized for forensic applications. The experimental setting combines the components for sample preparation, PCR amplification and Allele-specific Arrayed Primer Extension (AS-APEX) to form an integrated system to detect markers for eye color. The system contains a liquid handling sub-system (e.g., pumps), thermal cycling sub-system (e.g., Akonni Bladder Thermocycler), optical instrument (e.g., Akonni Reader), a disposable, integrated cartridge (i.e., Akonni TruTip, Akonni PCR/TruArray flow cell, microfluidic circuits, and microfluidic valves) and a cartridge docking station.

The six SNPs listed in Table 1 are used as test models for the experiment. These SNPs have been reported in the literature as major indicators of eye color.

TABLE 1

Six SNPs Identified as Major Determinants for Eye Color

| SNP-ID | Chr | Position | Gene | Common Allele/ Eye color | Minor Allele/ Eye color | Notes |
|---|---|---|---|---|---|---|
| rs12913832 | 15 | 26039213 | HERC2 | G/Blue | A/Brown | |
| rs1800407 | 15 | 25903913 | OCA2 | C/Brown | T/Blue | T/associated with Green/Hazel |
| rs12896399 | 14 | 91843416 | SLC24A4 | T/Blue | G/Brown | |
| rs16891982 | 5 | 33987450 | SLC45A2 | G/Blue | C/Brown | C/associated with Black hair |
| rs1393350 | 11 | 88650694 | TYR | G/Brown | A/Blue | |
| rs12203592 | 6 | 341321 | IRF4 | C/Brown | T/Blue | |

Sequence information for the SNPs was compiled and forward and reverse PCR primers were synthesized. Singleplex PCR reactions for each amplicon were tested and optimized. Systematic pooling of the primers in a multiplex format to produce a standard 6-plex PCR reaction for the eye color amplicons was achieved. This standard 6-plex PCR reaction was converted to a low temperature (LowTemp) 6-plex PCR reaction. LowTemp PCR involves using a chemical to supplement temperature annealing stringency. By adding formamide (a common PCR additive) to the master mix, the denaturing temperature was reduced to 85° C. instead of the normal 95° C. This strategy allows more choices of plastics and adhesives for our integrated cartridge; thereby lowering manufacturing costs. In addition, the lower temperature allows more material choices for the bladder thermocycler components and plumbing. In one embodiment, a single enzyme is used for both PCR and APEX.

FIG. 21A displays a microarray image and fluorescent intensities of gel spot signals for each amplicon generated in the LowTemp 6-plex PCR. All six amplicons were detected, with amplicon signal intensities exceeding the acceptable threshold for a positive call on the array. While relative signal intensities vary amongst the products, the signal intensities can be fine tuned by adjusting primer concentrations in the multiplex PCR and/or length of primers used for APEX.

In the APEX approach, primers are designed so that a single primer is immobilized within each gel element on the array such that the ending 3' base is at the SNP site. A separate primer is designed for each SNP to be detected. For instance, if there is a possibility for an A or a C at a certain SNP site, then a separate primer is designed for each, one ending in a 3' A and one in a 3' C. Extension by polymerase is inhibited if the 3' nucleotide of the primer is mismatched to the target. In the presence of the correct target and matched 3' base, polymerase incorporates fluorescently labeled nucleotides to produce the final signal.

Figure 21A:
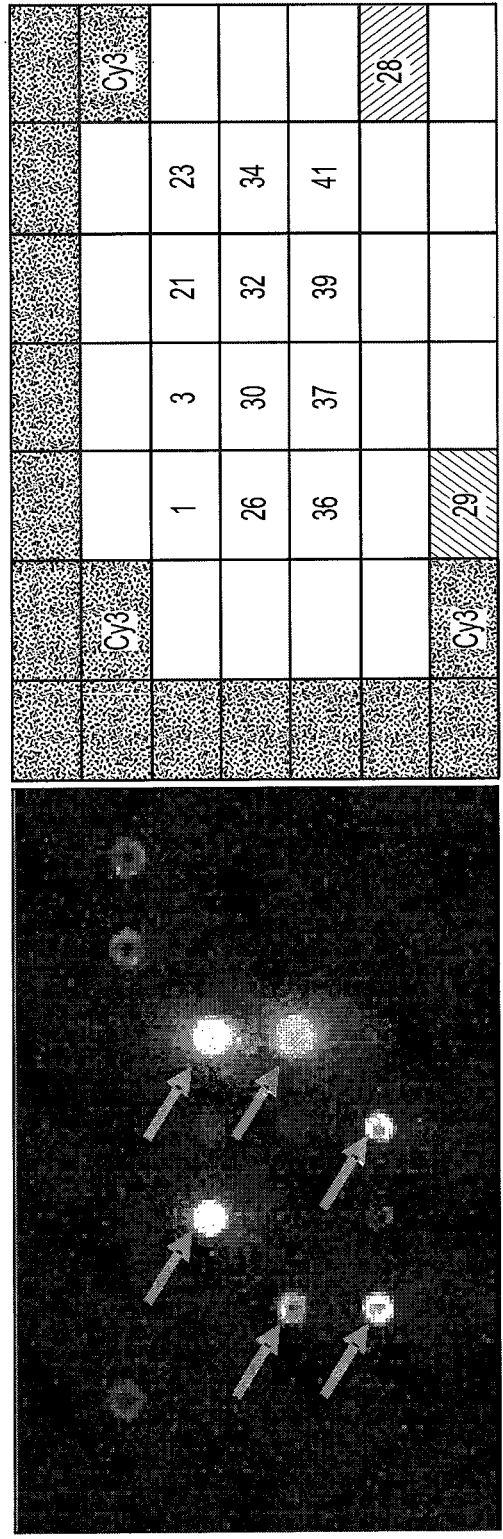
FIG. 21A shows the microarray results for 6-plex PCR products. The upper left panel is a microarray image with arrows pointing to the six PCR product generated in the multiplex PCR. The upper right panel is the microarray map. The lower panel shows probe number/primer identifier/fluorescent signal intensities for PCR product generated under three different annealing temperatures.
Figure 21B:
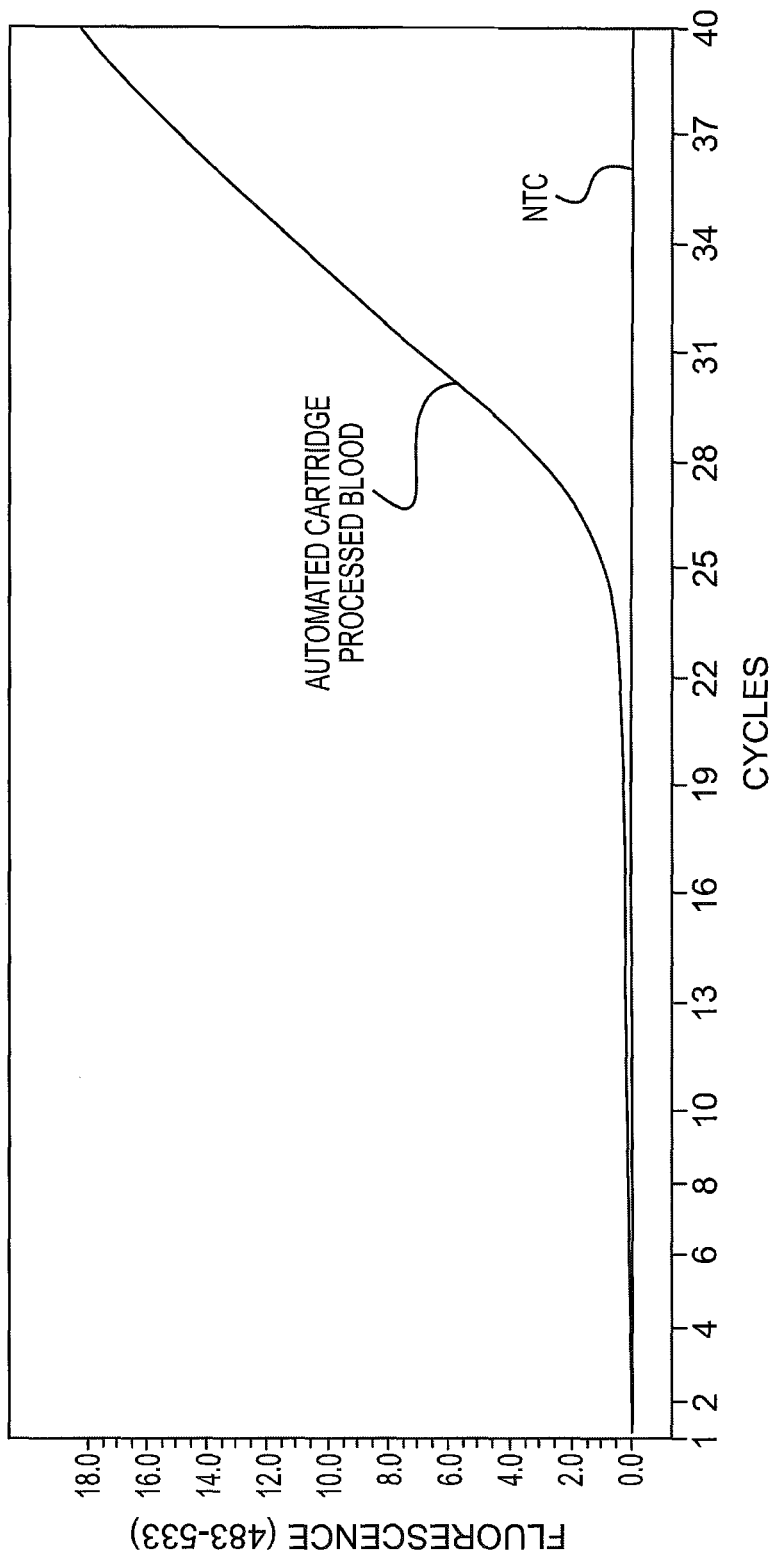
FIG. 21B is a diagram showing real-time PCR analysis of cartridge-purified blood DNA.

In one experiment, genomic DNA was purified from 50 ul blood sample using the integrated cartridge. In this process, all sample and sample waste along with all reagents/buffers that came in contact with the sample were maintained on the cartridge. Used reagents/buffers were moved and stored in the cartridge waste chamber. The entire process was performed under computer control. Real-time PCR results on extracted, purified DNA sample that was manually removed from the cartridge displayed a strong positive PCR signal (FIG. 21B). More importantly, this purified DNA was successfully used for manual PCR and APEX to call the correct genotype (Table 2). Briefly, automated, integrated cartridge-purified DNA was used for (manual PCR (20 ng DNA)/APEX typing. The fluorescent intensities of each primer on the array were imaged, and raw signal intensity data was used to generate primer (allele) signal ratio values for each SNP. The called genotype matched the genomic DNA sequencing results.

TABLE 2

Genotyping of blood samples using primer (allele) signal ratio values

| Sample ID | Description | Blood DNA Ratios Average | Average | Grand Average | Results |
|---|---|---|---|---|---|
| 50 | Rs1393350: G/A | 0.75 | 0.77 | 0.76 | A/G |
| 53 | Rs1393350: A/G | 1.33 | 1.30 | 1.32 | |
| 23 | Rs16891982: C/G | 5.33 | 5.48 | 5.40 | C |
| 24 | Rs16891982: G/C | 0.19 | 0.18 | 0.19 | |
| 77 | Rs1800407: G/A | 5.11 | 5.13 | 5.12 | G |
| 78 | Rs1800407: A/G | 0.20 | 0.20 | 0.20 | |
| 33 | Rs12913832: A/G | 3.62 | 3.64 | 3.63 | A |
| 34 | Rs12913832: G/A | 0.28 | 0.27 | 0.28 | |
| 66 | Rs12896399: G/T | 0.34 | 0.62 | 0.48 | T |
| 69 | Rs12896399: T/G | 2.91 | 1.62 | 2.26 | |
| 71 | Rs12203592: C/T | 31.55 | 10.83 | 21.19 | C |
| 73 | Rs12203592: T/C | 0.03 | 0.09 | 0.06 | |

Example 4

Software Development: DX3000 Automated Task Execution Program

A software program, designated DX3000 Automated Task Execution Program was created to control the integrated assay system. Code was written in Labview on a National Instruments industrial computer (NI 3110) to control the three major sub-systems (Fluidic Handling Sub-System, Thermocycler Sub-System, and Optical Sub-System). The NI 3110 has a dual-core processor where one core executes tasks for Windows and the other core executes tasks for a Real-Time operating system (OS). This architecture allows for the execution of high level Windows tasks such as managing the user-interface, serial communication and image processing, as well as low-level deterministic tasks such as control of the heaters, linear actuators, thermocycler pumps, and precisely timed events. The Real-Time OS communicates with the Ethercat I/O module, which scans analog input, analog output, and digital I/O modules.

Each of the three major sub-systems utilize resources from both the Windows and Real-Time OS and require communication between the two operating systems. Within the Windows environment a sequence of tasks, created by the user, is managed and communicated to the appropriate process on either the Real-Time OS or the Windows OS via shared variables. Tasks associated with the Fluidic Handling Sub-System include: change position of the selection valve(s), close/open cartridge valve(s), and dispense/aspirate with microfluidic pump. Tasks associated with the Thermocycler Sub-System include: warm up the thermocycler and initiate thermocycling. And tasks associated with the Optical Sub-System include: initiate APEX heating and acquire an image. Sequences can be saved and imported into the DX3000 Automated Task Execution Program.

The components, classified as being controlled by the Fluidic Handling Sub-System, include: 2 bi-directional pumps, 3 selection valves, and 8 linear actuators, which open and close the cartridge valves. The bi-directional pumps and the selection valves are controlled by a USB serial port. Serial commands are communicated to them via Labview drivers, developed by Global FIA. The control commands for the pump are direction, flow rate, volume and address, and the control commands for the selection valve include selection valve port number and address. Whereas these commands are executed entirely within Windows, the linear actuators are controlled primarily from the Real-Time Operating System. Linear actuators, available from Firgelli Technologies Inc. (Victoria, Canada) are controlled by an H bridge of 4 MOSFETs for each valve. Two digital I/O lines per actuator trigger the actuator to move forward, move backward, or remain at rest. When the actuator is at rest, no power is required. The actuators include an internal potentiometer to provide feedback of the position of the actuator arm. A calibration routine is used to determine the extents to which the actuator arm reaches, which correspond to a closed or an open position for the cartridge valves. A comparison algorithm is used to compare the desired with the actual location of the arm. The appropriate movements are executed to reach the desired location within a pre-determined tolerance window. Following the calibration routine, each, all, or some combination of the cartridge valves can be closed or opened as a task in the sequencer.

Figure 22:
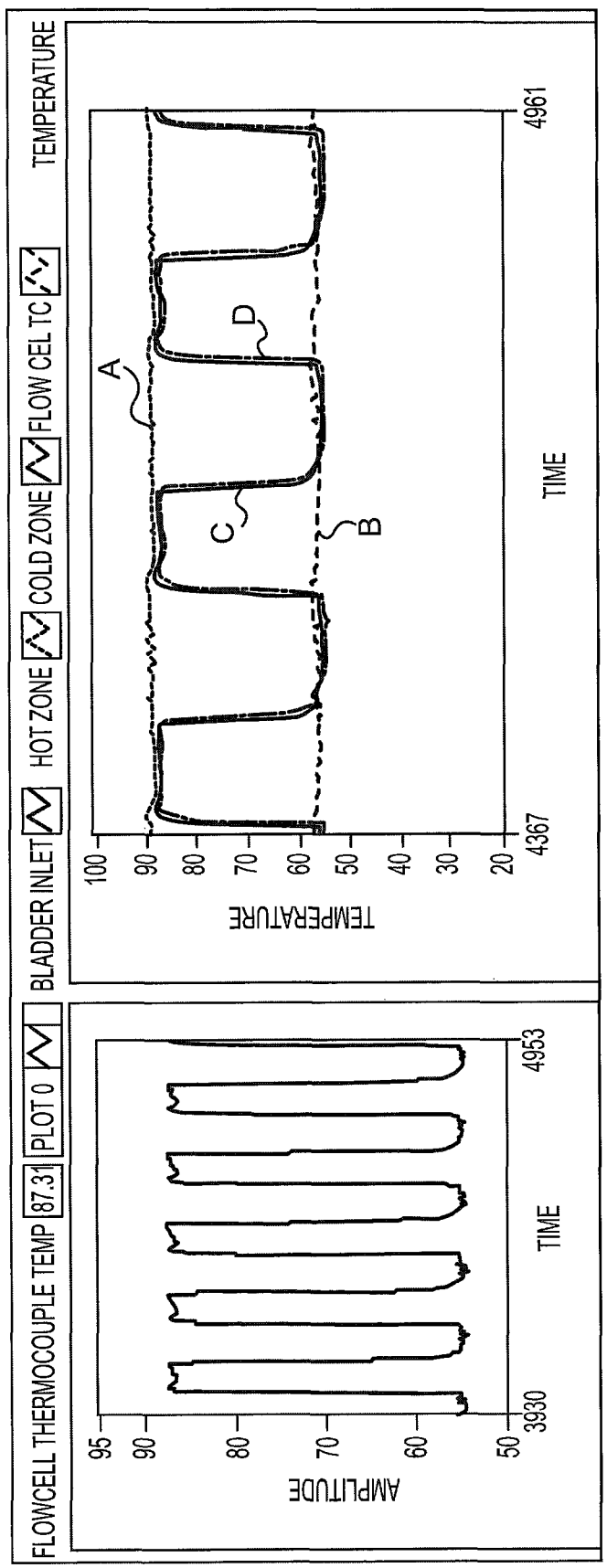
FIG. 22 shows thermocycling profile with PID pump and heater control. Line A shows the temperature of the hot zone, line B shows the cold zone, line C shows the temperature of a thermocouple sandwiched between the bladders, and line D shows the temperature of the working fluid just prior to entering the bladder.

The components, classified as being controlled by the Thermocycler Sub-System, include: 2 diaphragm pumps, 3 three-way valves, 3 coiled heaters (two for the hot zone and one for the cold zone), and a fan to provide cooling through a miniature radiator. Darlington BJT transistors source current to the diaphragm pumps in proportion to an analog output signal that is controlled by the DX3000 Automated Task Execution Program. Linearly proportional relays control the amplitude of an AC signal that powers the heaters and an AC fan for the radiator. An analog voltage output signal controls the output of these relays. Three in-line thermistors, exposed to the recirculating flow, are located after the hot zone and cold zone heaters and prior to the bladder. Two separate virtual processes control the recirculating temperature of the hot zone fluidic loop and the cold zone fluidic loop. These virtual processes include an algorithm for PID control of the temperature in the loop. The heater PID is used for a wide range of temperature control, but is slow responding. The pump flow rate PID has a narrow range of temperature control, but is fast responding. So, both PID loops are used to achieve rapid switching between the hot and cold zones with stable plateaus, as shown in FIG. 22. The radiator fan speed is typically maintained at 40% power.

The components, classified as being controlled by the Optical Sub-System, include: an LED, a camera, a heater, and an air pump. The LED, camera and air pump are turned on and off by solid state relays. A pulse width modulation algorithm controls the duty cycle of AC power to the heater using a solid state relay. The air pump flow rate is maintained at a constant rate. A thermocouple, internal to the heater, provides feedback to a PID virtual interface.

Example 5

Protein and Nucleic Acid Purification on the Same Cartridge

Figure 23:
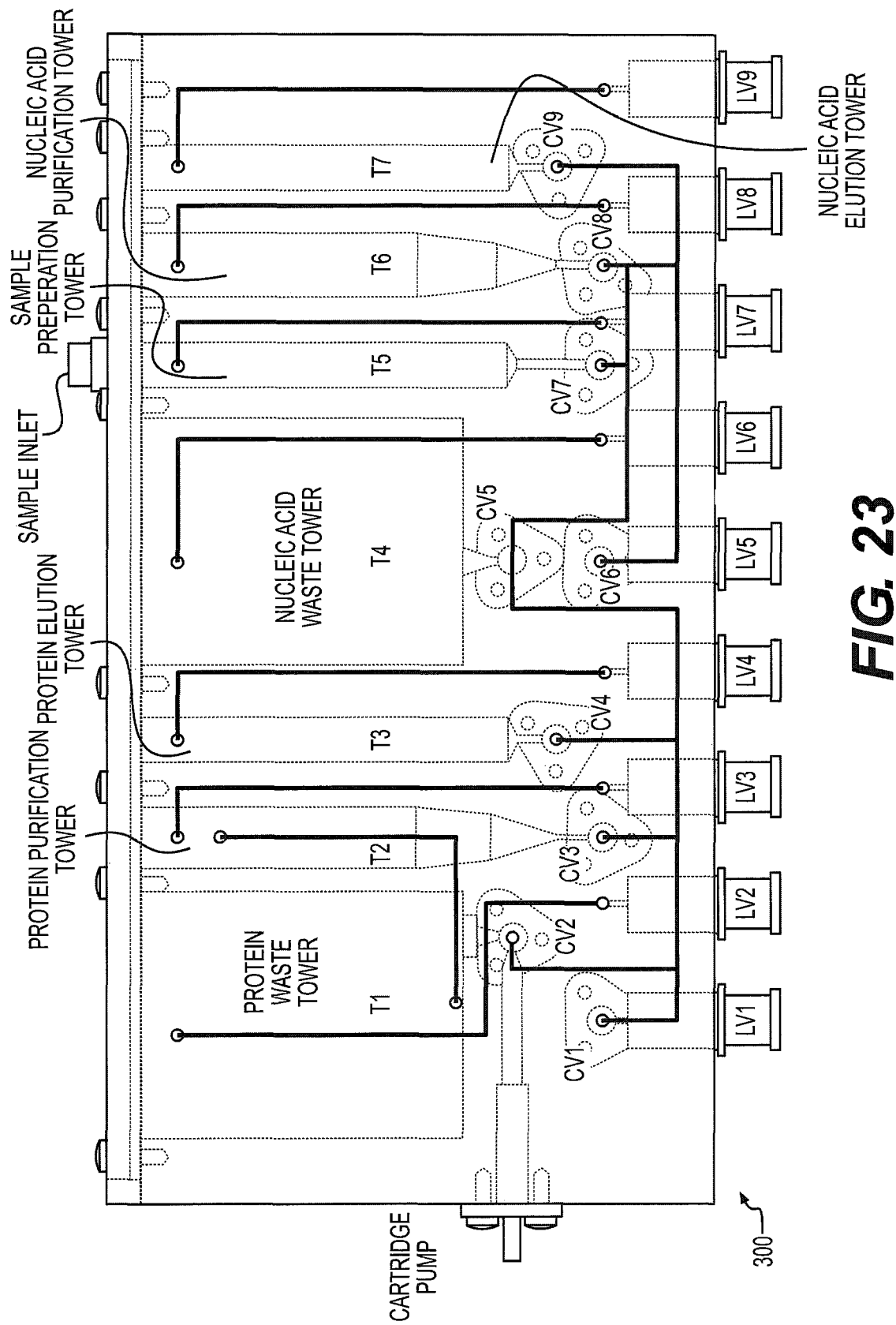
FIG. 23 is a drawing showing an embodiment of a dual-function integrated cartridge.

The integrated cartridge can be modified to contain both protein and nucleic acid purification capabilities. FIG. 23 shows an embodiment of a dual-function integrated cartridge 300. Briefly, the cartridge 300 contains a protein purification module and a nucleic acid purification module. The protein purification module includes a protein waste tower T1, a protein purification tower T2, a protein elution tower T3, cartridge pin valves CV1, CV2, CV3 and CV4 and Luer-activated valves LV1, LV2, LV3 and LV4. The nucleic acid purification module includes a nucleic acid waste tower T4, a sample preparation tower T5, a nucleic acid purification tower T6, a nucleic acid elution tower T7, cartridge pin valves CV5, CV6, CV7, CV8 and CV9, and Luer-activated valves LV5, LV6, LV7, LV8 and LV9.

In an embodiment, nucleic acid is purified via the following procedure:
1) A. Close all CVs
   B. Add 500 μL sample to T5 through sample inlet
   C. Open CV6 and CV7
   D. Add 500 μL cell lysis solution to T5 through LV5 (with LV7 venting to atmosphere)
2) Add air for mixing to T5 through LV5 (with LV7 venting to atmosphere)
3) Incubate for 5 minutes at room temperature
4) A. Close CV6, Open CV8 (CV7 remains open, CV8 will stay open until the start of Protein Purification protocol)
   B. Flow air through LV7 (with LV8 venting to atmosphere)
   C. Flow air through LV8 (with LV7 venting to atmosphere)
   Repeat Steps B & C five times. Mixture will flow back and forth from T5 to T6, ending in T6
5) A. Close CV7, Open CV2
   B. Flow air through LV8 (with LV2 venting to atmosphere) to push 1 mL of mixture into T1.
6) A. Open CV6, Close CV2
   B. Add wash to T6 through LV5 (with LV8 venting to atmosphere)
   C. Close CV6, Open CV7
   D. Flow air through LV8 (with LV7 venting to atmosphere)
   E. Flow air through LV7 (with LV8 venting to atmosphere)
   Repeat Steps D & E five times. Wash will flow back and forth from T5 to T6, ending in T6
   E. Close CV7, Open CV5
   F. Flow air through LV8 (with LV6 venting to atmosphere) to push wash into T4

7) A. Open CV6, Close CV5
   B. Add air to T6 through LV5 (with LV8 venting to atmosphere)
8) A. Add elution to T6 through LV5 (with LV8 venting to atmosphere)
   B. Close CV6, Open CV9
   C. Flow air through LV8 (with LV9 venting to atmosphere)
   D. Flow air through LV9 (with LV8 venting to atmosphere)
   Repeat Steps C & D five times. Elution will flow back and forth from T6 to T7, ending in T7

The proteins in the 1 ml sample mixture stored in T1 (see step 5B) is purified via the following procedure:
9) A. Open CV1 and CV2, close all other CVs
   B. Add protein binding solution to T1 through LV1 (with LV2 venting to atmosphere)
10) Add air for mixing to T1 through LV1 (with LV2 venting to atmosphere)
11) Incubate for 2 minutes at room temperature
12) A. Open CV3, Close CV1 (CV2 remains open, CV3 will stay open until the end of the protocol)
    B. Pull pump arm backwards to pull 250 μL of solution from T1 through T2 via the connecting channel (with LV2 & LV3 not venting)
    C. Push pump arm forward to push 250 μL of solution from T1 through T2 via the connecting channel (with LV2 & LV3 not venting)
    Repeat Steps B & C ten to fifteen times. Solution will flow in a single direction loop due to one-way check valve on cartridge, which is located directly above CV2 and directly below T1.
    D. Open CV5, Close CV2
    E. Flow air through LV3 to push solution into T4 (with LV6 venting to atmosphere)
    Note: Volume of Protein Waste Chamber (T1) is now full, so Nucleic Acid Waste Chamber is being used (T4)
    F. Open CV1, Close CV5
13) A. Add wash to T2 through LV1 (with LV3 venting to atmosphere)
    B. Open CV5, Close CV1
    C. Flow air through LV3 to push wash into T4 (with LV6 venting to atmosphere)
    D. Open CV1, Close CV5
    Repeat Steps A-D five times. Wash will be added to T2 and then flow into T4
14) Add air to T2 through LV1 (with LV3 venting to atmosphere)
15) Increase flow rate of air to blow out residual liquid
16) A. Add elution to T2 through LV1 (with LV3 venting to atmosphere)
    B. Close CV1, Open CV4
    C. Flow air through LV3 (with LV4 venting to atmosphere)
    D. Flow air through LV4 (with LV3 venting to atmosphere)
    Repeat Steps C & D five times. Elution will flow back and forth from T2 to T3, ending in T3

In one embodiment, the sample lysis solution is 6M guanidine isothiocyanate. In another embodiment, the protein binding solution is 0.1% trifluoroacetic acid.

Figure 24:
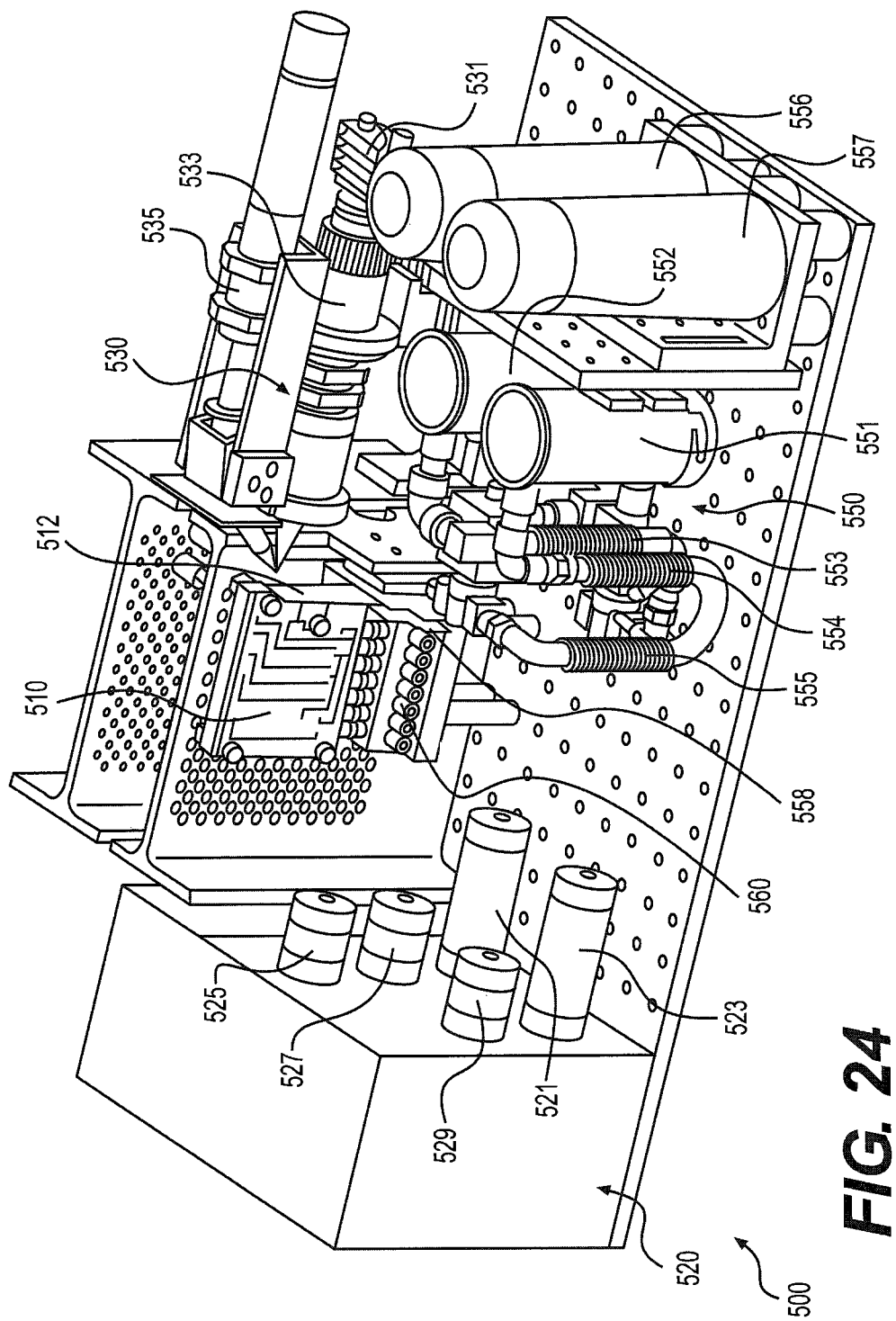
FIG. 24 is a schematic showing an embodiment of a complete MBSA system.

FIG. 24 shows a prototype MBSA system 500 that include an integrated cartridge 510 with a sample analysis unit 2 (i.e., a flow cell with an array chamber and a PCR chamber), a fluid control subsystem 520, an optical subsystem 530, a bladder thermocycler subsystem 550, and a fluidic manifold 560. In this embodiment, the fluid control subsystem 520 contains a setup capable of parallel processing of protein and nucleic acid in a dual-function integrated cartridge. The setup includes two pumps 521 and 523, and three selection valves 525, 527 and 529. One pump and one selection valve would be for nucleic acid extraction and the other pump and another selection valve for protein. The third selection valve would be used to open and close the vents. Such a setting would allow parallel processing of protein and nucleic acid simultaneously. The optical subsystem 530 includes a CCD camera 531, lens assembly 533 and illumination assembly 535. The bladder thermocycler subsystem 550 includes of two pumps 551 and 552, three heaters 553, 554 and 555 (two for the denaturing flow loop and one for the annealing/extension flow loop), two reservoirs 556 and 557 that serve as bubble traps and refilling access, and a bladder assembly 558 having two flexible bladders facing each other.

The present invention has been described in terms of specific embodiments incorporating details to facilitate the understanding of the principles of construction and operation of the invention. Such references herein to specific embodiments and details thereof are not intended to limit the scope of the claims appended hereto. It will be apparent to those skilled in the art that modifications may be made in the embodiment chosen for illustration without departing from the spirit and scope of the invention. All the references cited in the specification are hereby incorporated by reference in their entirety.

What is claimed is:

1. An integrated cartridge for sample processing and analysis, comprising:
    a sample purification chamber configured to receive a replaceable sample purification unit containing a housing and an extraction filter inside the housing, wherein the extraction filter is a silica filter that specifically binds to an analyte;
    a sample analysis unit in fluid communication with the sample purification chamber, wherein the sample analysis unit comprises a microarray chamber comprising a microarray for analysis of analyte eluted from the silica filter; and
    a plurality of pin valves that control liquid movement within the cartridge.

2. The integrated cartridge of claim 1, further comprising a waste chamber.

3. The integrated cartridge of claim 1, wherein the microarray chamber is configured to perform an amplification reaction within the chamber.

4. The integrated cartridge of claim 1, wherein the one or more plurality of pin valves are controlled by one or more linear actuators.

5. The integrated cartridge of claim 1, further comprising microfluidic channels that facilitate fluid movement within the integrated cartridge, wherein interior surfaces of the microchannels are fully or partially covered or coated with a hydrophilic film to reduce bubble trapping inside the microfluidic channels.

6. The integrated cartridge of claim 5, wherein the microfluidic channels have diameters that are sufficiently large to reduce backpressure and enable reproducible injection molded features.

7. The integrated cartridge of claim 1, wherein the microarray is a DNA array.

8. The integrated cartridge of claim 1, wherein the microarray is a protein or peptide array.

9. The integrated cartridge of claim 1, wherein the microarray is an antibody array.

10. The integrated cartridge of claim 1, wherein the plurality of pin valves are electronically controlled.

11. The integrated cartridge of claim 10, wherein the plurality of pin valves are controlled by a linear actuator panel.

12. An integrated cartridge for sample processing and analysis, comprising:
    means configured to receive a replaceable sample purification unit containing a housing and an extraction filter inside the housing, wherein the extraction filter comprises a silica filter that specifically binds to nucleic acids;
    a sample analysis unit in fluid communication with the sample purification chamber, wherein the sample analysis unit comprises a microarray chamber comprising a DNA microarray for analysis of nucleic acids eluted from the silica filter; and
    a plurality of pin valves that control liquid movement within the cartridge.

\* \* \* \* \*